United States Patent
Shandas et al.

(10) Patent No.: US 9,820,842 B2
(45) Date of Patent: Nov. 21, 2017

(54) MEDICAL FABRIC WITH INTEGRATED SHAPE MEMORY POLYMER

(71) Applicant: The Regents of the University of Colorado, a Body Corporate, Denver, CO (US)

(72) Inventors: Robin Shandas, Boulder, CO (US); Michael Zimkowski, Aurora, CO (US)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 137 days.

(21) Appl. No.: 14/648,640

(22) PCT Filed: Dec. 2, 2013

(86) PCT No.: PCT/US2013/072693
§ 371 (c)(1),
(2) Date: May 29, 2015

(87) PCT Pub. No.: WO2014/085827
PCT Pub. Date: Jun. 5, 2014

(65) Prior Publication Data
US 2015/0299359 A1 Oct. 22, 2015

Related U.S. Application Data

(60) Provisional application No. 61/732,147, filed on Nov. 30, 2012.

(51) Int. Cl.
*A61B 17/08* (2006.01)
*A61F 2/00* (2006.01)
(Continued)

(52) U.S. Cl.
CPC .......... *A61F 2/0063* (2013.01); *A61L 31/048* (2013.01); *C08F 220/18* (2013.01);
(Continued)

(58) Field of Classification Search
CPC ...... C08F 2220/1825; C08F 2222/1013; C08F 222/22; C08F 220/18; A61L 31/048;
(Continued)

(56) References Cited

U.S. PATENT DOCUMENTS

| 5,128,197 A | 7/1992 | Kobayashi et al. |
| 5,824,082 A | 10/1998 | Brown |

(Continued)

FOREIGN PATENT DOCUMENTS

| WO | 2008/051254 A1 | 5/2008 |
| WO | 2012/034126 A1 | 3/2012 |

OTHER PUBLICATIONS

Gall, Ken et al., "Thermomechanics of the Shape Memory effect in polymers for biomedical applications", J. Biomed Mater Res 73A, 2005; 73(3), (www.interscience.wiley.com) Wiley Int Science, pp. 339-348.

*Primary Examiner* — Katherine M Shi
(74) *Attorney, Agent, or Firm* — Dorsey & Whitney LLP

(57) ABSTRACT

Formulations of shape memory polymer (SMP) are integrated with several existing clinically available medical fabrics. The SMP portion of a SMP integrated fabric can be fabricated in varying thicknesses with the minimum thickness determined by the thickness of the underlying fabric and up to almost any thickness. Integration of the SMP with the base fabrics does not alter the shape memory functionality of the SMP. The design tools for controlling activation rate for traditional SMP materials thus apply to SMP integrated fabrics. SMP integrated fabrics may also be steam sterilized without loss of shape memory functionality.

14 Claims, 24 Drawing Sheets

(51) Int. Cl.
*C08F 220/18* (2006.01)
*A61L 31/04* (2006.01)

(52) U.S. Cl.
CPC .............. *A61F 2002/0072* (2013.01); *A61F 2210/0019* (2013.01); *A61F 2240/001* (2013.01); *A61L 2400/16* (2013.01)

(58) Field of Classification Search
CPC .............. A61L 2400/16; C08L 33/08; A61F 2002/0072; A61F 2210/0019; A61F 2240/001; A61F 2/0063
USPC ......................................................... 606/151
See application file for complete search history.

(56) References Cited

U.S. PATENT DOCUMENTS

| | | |
|---|---|---|
| 6,176,271 B1 | 1/2001 | Sayers |
| 6,388,043 B1 | 5/2002 | Langer et al. |
| 6,517,584 B1 | 2/2003 | Lecalve |
| 6,669,706 B2 | 12/2003 | Schmitt et al. |
| 7,001,328 B1 | 2/2006 | Barofsky et al. |
| 8,226,686 B2 | 7/2012 | Deitch et al. |
| 2002/0103494 A1 | 8/2002 | Pacey |
| 2004/0191556 A1 | 9/2004 | Jardine |
| 2005/0250978 A1 | 11/2005 | Kammerer |
| 2006/0041089 A1 | 2/2006 | Mather et al. |
| 2007/0125247 A1 | 6/2007 | Kunstmann et al. |
| 2007/0179529 A1 | 8/2007 | Doyle |
| 2007/0265710 A1 | 11/2007 | Brown et al. |
| 2008/0195123 A1 | 8/2008 | Gainor et al. |
| 2009/0171376 A1 | 7/2009 | Burton et al. |
| 2009/0204129 A1 | 8/2009 | Fronio |
| 2009/0248141 A1 | 10/2009 | Shandas et al. |
| 2009/0270999 A1 | 10/2009 | Brown |
| 2010/0104608 A1 | 4/2010 | Abuzaina et al. |
| 2010/0122698 A1 | 5/2010 | Shaffer et al. |
| 2010/0189764 A1 | 7/2010 | Thomas et al. |
| 2010/0210745 A1 | 8/2010 | McDaniel et al. |
| 2011/0144227 A1 | 6/2011 | Bowman et al. |
| 2011/0152897 A1 | 6/2011 | Bates |
| 2011/0184439 A1 | 7/2011 | Anderson et al. |
| 2011/0238094 A1 | 9/2011 | Thomas et al. |
| 2011/0270284 A1 | 11/2011 | Beauchamp |
| 2011/0282365 A1 | 11/2011 | Hadba et al. |
| 2012/0010636 A1 | 1/2012 | Boey et al. |
| 2012/0071905 A1 | 3/2012 | Girard et al. |

MEDICAL FABRIC WITH INTEGRATED SHAPE MEMORY POLYMER

CROSS REFERENCE TO RELATED APPLICATIONS

The present application claims priority to U.S. Provisional Patent Application No. 61/732,147 filed 30 Nov. 2012 entitled "Medical fabric with integrated shape memory polymer," which is hereby incorporated herein by reference in its entirety.

The present application is related to the following applications: Patent Cooperation Treaty Application No. PCT/US2011/051239 filed 12 Sep. 2011 entitled "Medical fabric with integrated shape memory polymer"; U.S. patent application Ser. No. 12/988,983 filed 5 Jan. 2011 entitled "Thiol-vinyl and thiol-yne systems for shape memory polymers"; U.S. patent application Ser. No. 12/295,594 filed 30 Sep. 2008 entitled "Shape memory polymer medical devices"; Patent Cooperation Treaty Application No. PCT/US2006/060297 filed 27 Oct. 2006 entitled "A polymer formulation, a method of determining a polymer formulation, and a method of determining a polymer fabrication" and each is hereby incorporated herein by reference in its entirety.

TECHNICAL FIELD

The technology described herein relates generally to surgical or medical repair materials and more specifically to the use of shape memory materials in surgical or medical repair materials.

BACKGROUND

Shape memory materials are defined by their capacity to recover a predetermined shape after significant mechanical deformation. The shape memory effect is typically initiated by a change in temperature and has been observed in metals, ceramics, and polymers. From a macroscopic point of view, the shape memory effect in polymers differs from ceramics and metals due to the lower stresses and larger recoverable strains achieved in polymers.

Several existing devices have incorporated shape memory metals into a hernia patch. For example, in PCT Patent Application Publication No. WO 2012/034126 a shape memory polymer is integrated into a medical fabric such as a hernia patch. In U.S. Pat. No. 6,669,735, a combination of synthetic mesh is supported on a ring of shape memory metal alloy for use as a hernia repair patch. Similarly, another hernia repair patch is described in U.S. Patent Application Publication No. 2007/0265710 that uses a shape memory alloy (i.e., Nitinol) or shape memory polymer (Polynorbornene) as a frame for the synthetic mesh of the patch.

The information included in this Background section of the specification, including any references cited herein and any description or discussion thereof, is included for technical reference purposes only and is not to be regarded subject matter by which the scope of the invention is to be bound.

SUMMARY

Disclosed herein are shape memory polymer (SMP) integrated fabrics that may be used for a variety of medical applications. For example, the SMP-integrated fabrics disclosed herein may be used in a hernia repair patch. Numerous formulations of SMP are integrated with several existing clinically available medical fabrics including, for example: polyester mesh, polypropylene mesh, polypropylene derivates, polytetrafluoroethylene (PTFE or GoreTex®), expanded polytetrafluoroethylene (ePTFE), Dacron®, and combinations thereof, giving these existing materials unique properties that address several unmet clinical needs. The SMP portion of a SMP-integrated fabric can be fabricated in varying thicknesses with the minimum thickness determined by the thickness of the underlying fabric and up to almost any thickness.

In one implementation, a shape memory polymer integrated medical fabric for use in a surgical procedure is disclosed. The integrated fabric includes a medical fabric and a shape memory polymer integrated with the medical fabric to provide a deformable and reformable structure to the integrated fabric upon placement in vivo. The surgical procedure may be repair of a hernia and the integrated medical fabric is a hernia repair patch. The shape memory polymer may include thiol and/or vinyl monomers or oligomers. The shape memory polymer may further include acrylate or methacrylate functional groups. The shape memory polymer may be a 20 wt % PEGDMA with a $M_n=1000$ and remainder tert-butyl acrylate with 0.2-0.3 wt photoinitiator (2,2 dimethoxy-2-phenylacetopenone).

In another implementation, a shape memory polymer integrated medical fabric for use in a surgical procedure is disclosed. The integrated fabric includes a medical fabric and a shape memory polymer integrated with the medical fabric to provide a glass transition temperature close to body temperature, mechanical strength similar to the medical fabric alone, high strain to failure, and the added functionality of automatic unrolling as the mesh reaches body temperature.

In another implementation, a method of forming a shape memory polymer-integrated fabric is disclosed. The method may include providing a medical fabric and placing the medical fabric in a glass mold. A shape memory polymer of a desired formulation is injected into the mold. The shape memory polymer is exposed to ultraviolet light to cure the shape memory polymer. The integrated medical fabric with the cured shape memory polymer is then removed or released from the mold. In some implementations, a gas such as nitrogen or argon may be injected into the mold to assist the curing process. Also, in some implementations, a mask may be placed on or a wax layer may be placed adjacent to the medical fabric before applying the shape memory polymer to prevent the shape memory polymer from integrating with certain portions of the medical fabric covered by the mask or adjacent to the wax. The method may also include sterilization of the SMP-integrated fabric by steam or chemical sterilization.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of the present invention is provided in the following written description of various embodiments of the invention, illustrated in the accompanying drawings, and defined in the appended claims.

DETAILED DESCRIPTION

Figure 1A:
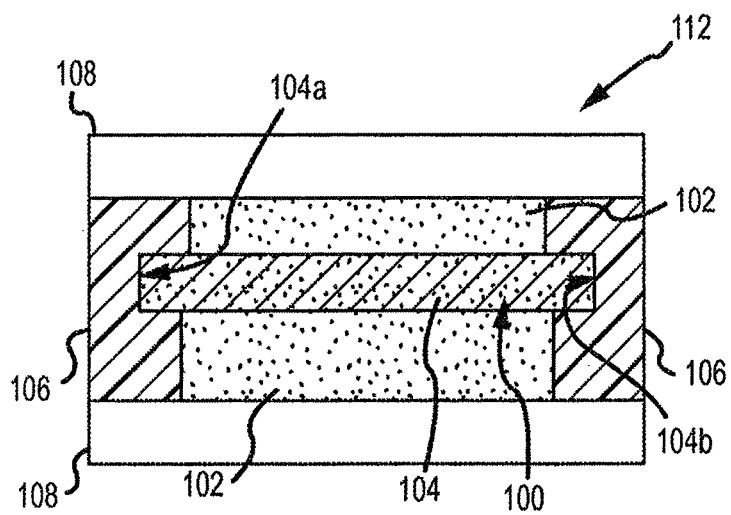
FIG. 1A is a schematic cross-section view of an exemplary implementation of a mold set-up for curing a SMP-integrated fabric.
Figure 1B:
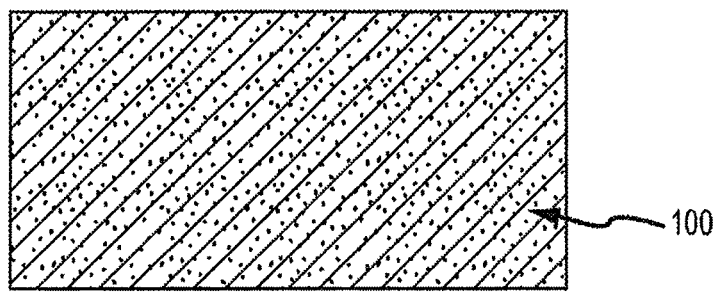
FIG. 1B is a schematic top plan view of a SMP-integrated fabric formed by the mold set-up of FIG. 1A.

As disclosed herein, a shape memory polymer (SMP) or more than one SMP may be integrated into a fabric to create a SMP-integrated fabric. Integration of the SMP with the traditional fabrics does not alter the shape memory functionality of the SMP. This indicates that all of the design tools for controlling activation rate for traditional SMP materials apply to SMP-integrated fabrics. SMP-integrated fabrics may also be steam sterilized without loss of shape memory functionality. Other sterilization techniques are also possible.

In certain exemplary implementations, a variety of acrylate based shape memory polymers are used in a hernia repair patch. These shape memory polymers are advantageous over existing hernia patches because of the flexibility that exists in customizing the material properties and the shape memory effects, for example, variable stiffness and activation time. The material disclosed herein improves upon prior hernia patch designs by using a customizable shape memory polymer as opposed to a rigid shape memory metal alloy or non-customizable polymer. The shape memory polymer formulations may be tailored so that the temperature of activation, the time of activation, the rate of activation, and the mechanical stiffness can be varied based on application requirements.

In some exemplary embodiments, the amounts of shape memory polymer and the surgical mesh material (e.g., polyester (polyethylene terephthalate), polypropylene, polypropylene derivates, Dacron®, polytetrafluoroethylene (PTFE or Goretex®), expanded polytetrafluoroethylene (ePTFE), or combinations thereof) are varied to achieve varying levels of tissue incorporation and/or adhesion with the SMP hernia repair patch. For example, the surgical mesh material may be completely encapsulated in shape memory polymer, which would inhibit mesh integration into tissue. Alternatively, only one side of the mesh material or only a section of the mesh material may be coated with the shape memory polymer, which would allow the remaining mesh to be absorbed into the tissue. Further, the porosity of the shape memory polymer material may be varied to thereby allow even greater amounts of mesh-tissue integration.

Shape Memory Polymers

Basic thermomechanical response of shape memory polymer (SMP) materials is defined by four critical temperatures. The glass transition temperature, $T_g$, is typically represented by a transition in modulus-temperature space and can be used as a reference point to normalize temperature. SMPs offer the ability to vary $T_g$ over a temperature range of several hundred degrees by control of chemistry or structure. The predeformation temperature, $T_d$, is the temperature at which the polymer is deformed into its temporary shape. Depending on the required stress and strain level, the initial deformation at $T_d$ can occur above or below $T_g$. The storage temperature, $T_s$, represents the temperature in which no shape recovery occurs and is equal to or below $T_d$. At the recovery temperature, $T_r$, the shape memory effect is activated, which causes the material to recover its original shape, and is typically in the vicinity of $T_g$. Recovery can be accomplished isothermally by heating to a fixed $T_r$ and then holding, or by continued heating up to and past $T_r$. From a macroscopic viewpoint, a polymer will demonstrate a useful shape memory effect if it possesses a distinct and significant glass transition and a large difference between the maximum achievable strain, $\epsilon_{max}$, during deformation and permanent plastic strain after recovery, $\epsilon_p$. The difference $\epsilon_{max}-\epsilon_p$ is defined as the recoverable strain, $\epsilon_{recover}$ while the recovery ratio is defined as $\epsilon_{recover}/\epsilon_{max}$.

The microscopic mechanism responsible for shape memory in polymers depends on both chemistry and structure. The primary driving force for shape recovery in polymers is the low conformational entropy state created and subsequently frozen during the thermomechanical cycle. If the polymer is deformed into its temporary shape at a temperature below $T_g$, or at a temperature where some of the hard polymer regions are below $T_g$, then internal energy restoring forces will also contribute to shape recovery. In either case, to achieve shape memory properties, the polymer must have some degree of chemical crosslinking to form a "memorable" network or must contain a finite fraction of hard regions serving as physical crosslinks.

Shape memory polymer materials may be used for a wide variety of applications. Their ability to recover strains imparted upon them, in a manner that is different than pure thermal expansion, due to an external stimulus, makes SMP materials well suited for many applications, such as biological and general mechanical. The external stimulus that activates SMPs may be heat, light, or other stimuli known to those having skill in the art. SMPs which use heat as an external stimulus often have temperatures at which transition occurs.

A transition temperature can be a property of a material (e.g., SMP, thermoplastic, thermoset). A transition temperature may be defined through a number of methods/measurements and different embodiments may use any of these different methods/measurements. For example, a transition temperature may be defined by a temperature of a material at the onset of a transition ($T_{onset}$), the midpoint of a transition, or the completion of a transition. As another example, a transition temperature may be defined by a temperature of a material at which there is a peak in the ratio of a real modulus and an imaginary modulus of a material (e.g., peak tan-δ). It should be noted that the method of measuring the transition temperature of a material may vary, as may the definition of steps taken to measure the transition temperature (e.g., there may be other definitions of tan-δ).

A transition temperature may be related to a number of processes or properties. For example, a transition temperature may relate to a transition from a stiff (e.g., glassy) behavior to a rubbery behavior of a material. As another example, a transition temperature may relate to a melting of soft segments of a material. A transition temperature may be represented by a glass transition temperature ($T_g$), a melting point, or another temperature related to a change in a process in a material or another property of a material.

In addition, molecular and/or microscopic processes, including those processes around a transition temperature, may be related to the macroscopic properties of the material. From a macroscopic viewpoint, as embodied in a modulus-temperature graph, a polymer's shape memory effect may possess a glass transition region, a modulus-temperature plateau in the rubbery state. A polymer's shape memory effect may include, as embodied in a stress-strain graph, a difference between the maximum achievable strain, $\epsilon_{max}$, during deformation and permanent plastic strain after recovery, $\epsilon_p$. The difference $\epsilon_{max}-\epsilon_p$ may be considered the recoverable strain, $\epsilon_{recover}$, while the recovery ratio (or recovery percentage) may be considered $\epsilon_{recover}/\epsilon_{max}$.

Figure 4:
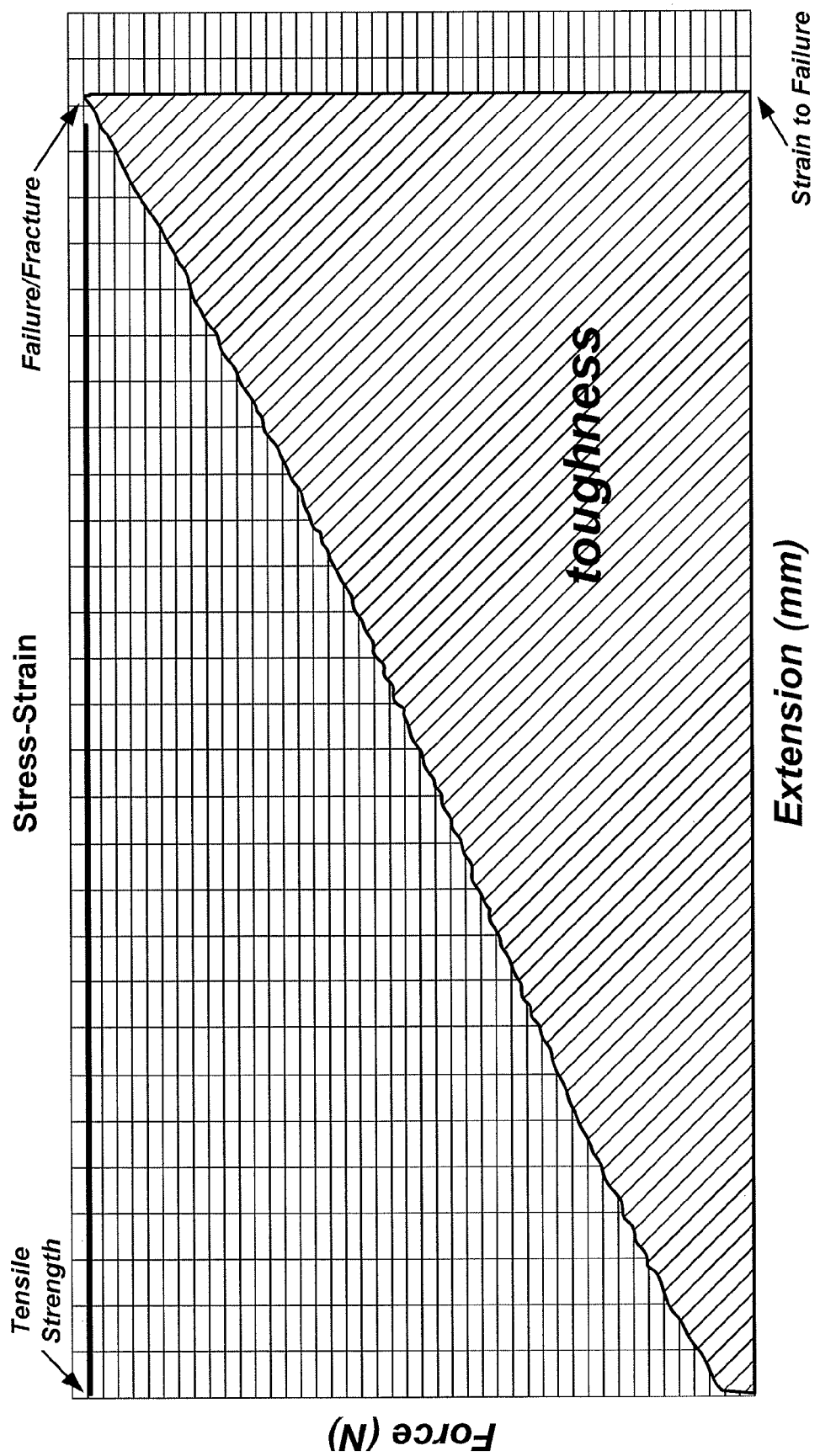
FIG. 4 is a graphical representation of force versus extension.

A polymer's shape memory effect may also be described in terms of tensile strength and/or strain to failure (see FIG. 4). As described in more detail below in Example 3, uniaxial tensile testing may be performed on shape memory polymer formulations alone or SMP formulations integrated with a medical fabric to determine tensile strength and strain to failure. Testing may be performed according to standards in the art, for example ASTM Test Method D638-03 using Type V specimen geometry.

A polymer's shape memory effect may also be described in terms of the mechanical property "toughness". As shown in FIG. 4, toughness is the area under a stress-strain curve, and may be quantified by strain to failure and tensile strength. A shape memory polymer may be described as tough or tougher than another shape memory polymer if it exhibits high strain to failure and good tensile strength. For the purposes of use in a medical fabric application, it is desirable to identify a tough shape memory polymer having a desired glass transition temperature and also having an unfolding strength, which facilitates functionality of the SMP. There is nothing chemically predictive of the combination of such qualities and determination is subject to trial and error of formulations anticipated to exhibit shape memory properties.

The properties of SMPs can be controlled by changing the formulation of the SMP, or by changing the treatment of the SMP through polymerization and/or handling after polymerization. The techniques of controlling SMP properties rely on an understanding of how SMP properties are affected by these changes and how some of these changes may affect more than one property. For example, changing the percentage weight of a cross-linker in a SMP formulation may change both a transition temperature of the SMP and a modulus of the SMP. In one embodiment, changing the percentage weight of a cross-linker will affect the glass transition temperature and the rubbery modulus of an SMP. In another embodiment, changing the percentage weight of cross-linker will affect a recovery time characteristic of the SMP.

Some properties of a SMP may be interrelated such that controlling one property has a strong or determinative effect on another property, given certain assumed parameters. For example, the force exerted by a SMP against a constraint after the SMP has been activated may be changed through control of the rubbery modulus of the SMP. Several factors, including a level of residual strain in the SMP enforced by the constraint, will dictate the stress applied by the SMP, based on the modulus of the SMP. The stress applied by the SMP is related to the force exerted on the constraint by known relationships.

Although an understanding of the properties of each SMP may serve as a starting point for the design of a SMP formulation predicted to have a set of desired characteristics, the combination of more than one SMP, the introduction of other constituents (e.g. cross-linkers, as described in more detail below), the properties of those other constituents, the polymerization process, and/or other aspects of making a SMP-integrated fabric often lead to unpredictable or unexpected results. An evaluation of known SMP component properties, empirically-derived relationships between component properties and SMP formulation properties, and/or theoretical models of those relationships may lead to a predicted characteristic or set of characteristics for a given SMP formulation. In vitro and in vivo experimentation reveals that SMP formulations and SMP-integrated fabrics often do not possess the expected characteristics. In vitro and in vivo experimentation is required to determine how a given SMP and its corresponding SMP-integrated fabric will perform in vitro and in vivo, respectively.

Specialized formula combinations (described in more detail below) provide enhanced properties for specific applications. For example, some applications may benefit from high strain-to-failure, where one or more formulations excel. Other applications may benefit from lower transition temperature, where one or more formulations excel. Additionally, some SMP formulations are designed to provide enhanced characteristics in multiple mechanical relationships.

Examples of constituent parts of the SMP formulation include monomers, multi-functional monomers, cross-linkers, initiators (e.g., photo-initiators), and dissolving materials (e.g., drugs, salts). Two commonly included constituent parts are a linear chain and a cross-linker, each of which are common organic compounds such as monomers, multi-functional monomers, and polymers.

A cross-linker (or "crosslinker"), as used herein, may mean any compound comprising two or more functional groups (e.g., acrylate, methacrylate), such as any polyfunctional monomer. For example, a multi-functional monomer is a poly ethylene glycol (PEG) molecule comprising at least two functional groups, such as di-methacrylate (DMA), or the combined molecule of PEGDMA. The percentage weight of cross-linker indicates the amount of the polyfunctional monomers placed in the mixture prior to polymerization (e.g., as a function of weight), and not necessarily any direct physical indication of the as-polymerized "cross-link density."

Because SMP material requires both a thermal transition and a form of crosslinking to possess shape-memory characteristics, the polymer is typically synthesized from a linear chain building mono-functional monomer (tert-butyl acrylate) and a crosslinking di-functional monomer (PEGDMA). Because the crosslinking monomer has two methacrylate groups, one at each end, it is possible to connect the linear chains together. This linear monomer portion can be used to help control the glass transition temperature of the network as well as its overall tendency to interact with water. Thus, the linear portion of the network remains an important and tailor-able portion of the composition.

A mono-functional monomer, for example tert-butyl acrylate (tBA), may comprise from about 60 wt % to about 99 wt % of a shape memory polymer composition. In some embodiments, tBA comprises from about 65 wt % to about 90 wt % of a shape memory polymer composition. In other embodiments, tBA comprises from about 70 wt % to about 90 wt % of a shape memory polymer composition. In other embodiments, tBA comprises from about 70 wt % to about 85 wt % of a shape memory polymer composition. In still other embodiments, tBA comprises from about 75 wt % to about 85 wt % of a shape memory polymer composition.

In some embodiments, tBA comprises more than 60 wt % of a shape memory polymer composition. In other embodiments, tBA comprises more than 65 wt %, more than 70 wt %, more than 75 wt %, more than 80 wt %, more than 85 wt %, more than 90 wt %, or more than 95 wt % of a shape memory polymer composition.

In some embodiments, tBA comprises less than 99 wt % of a shape memory polymer composition. In other embodiments, tBA comprises less than 95 wt %, less than 90 wt %, less than 85 wt %, less than 80 wt %, less than 75 wt %, less than 70 wt %, or less than 65 wt % of a shape memory polymer composition.

In some embodiments, tBA comprises about 65 wt % of a shape memory polymer composition. In other embodiments, tBA comprises about 75 wt %, about 76 wt %, about 77 wt %, about 78 wt %, about 79 wt %, about 80 wt %, or about 90 wt % of a shape memory polymer composition.

Butyl acrylate (nBA) may comprise from about 0 wt % to about 20 wt % of a shape memory polymer composition. In some embodiments, nBA comprises more than 0 wt % of a shape memory polymer composition. In other embodiments, nBA comprises more than 5 wt %, more than 10 wt %, or more than 15 wt % of a shape memory polymer composition.

In some embodiments, nBA comprises less than 20 wt % of a shape memory polymer composition. In other embodiments, nBA comprises less than 15 wt %, less than 10 wt %, or less than 5 wt % of a shape memory polymer composition.

In some embodiments, nBA comprises about 0 wt % of a shape memory polymer composition. In other embodiments, nBA comprises about 4 wt %, about 5 wt %, about 10 wt %, or about 15 wt % of a shape memory polymer composition.

Isobutyl acrylate (iBA) may comprise from about 0 wt % to about 10 wt % of a shape memory polymer composition. iBA may comprise from about 0.5 wt % to about 4 wt % of a shape memory polymer composition. In some embodiments, iBA comprises more than 0 wt % of a shape memory polymer composition. In other embodiments, iBA comprises more than 2 wt %, more than 4 wt %, more than 6 wt %, or more than 8 wt % of a shape memory polymer composition.

In some embodiments, iBA comprises less than 10 wt % of a shape memory polymer composition. In other embodiments, iBA comprises less than 8 wt %, less than 6 wt %, less than 4 wt %, or less than 2 wt % of a shape memory polymer composition.

In some embodiments, iBA comprises about 0 wt % of a shape memory polymer composition. In other embodiments, iBA comprises about 2 wt %, about 4 wt %, about 6 wt %, or about 8 wt % of a shape memory polymer composition.

Ethylhexyl acrylate (EHA) may comprise from about 0 wt % to about 10 wt % of a shape memory polymer composition. EHA may comprise from about 0.5 wt % to about 7 wt % of a shape memory polymer composition, or from about 0.5 wt % to about 4 wt % of a shape memory polymer composition. In some embodiments, EHA comprises more than 0 wt % of a shape memory polymer composition. In other embodiments, EHA comprises more than 2 wt %, more than 4 wt %, more than 6 wt %, or more than 8 wt % of a shape memory polymer composition.

In some embodiments, EHA comprises less than 10 wt % of a shape memory polymer composition. In other embodiments, EHA comprises less than 8 wt %, less than 6 wt %, less than 4 wt %, or less than 2 wt % of a shape memory polymer composition.

In some embodiments, EHA comprises about 0 wt % of a shape memory polymer composition. In other embodiments, EHA comprises about 2 wt %, about 3.5 wt %, about 6 wt %, or about 8 wt % of a shape memory polymer composition.

One or more mono-functional monomers may be cross-linked with a multi-functional monomer via photopolymerization with a photoinitiator, for example 2,2 dimethoxy-2-phenylacetopenone (DMPA). DMPA may comprise from about 0.05 wt % to about 1.0 wt % of a shape memory polymer composition. In some embodiments, DMPA comprises more than 0.05 wt % of a shape memory polymer composition. In other embodiments, DMPA comprises more than 0.1 wt %, more than 0.2 wt %, more than 0.4 wt %, more than 0.6 wt %, or more than 0.8 wt % of a shape memory polymer composition.

In some embodiments, DMPA comprises less than 1.0 wt % of a shape memory polymer composition. In other embodiments, DMPA comprises less than 0.8 wt %, less than 0.6 wt %, less than 0.4 wt %, less than 0.2 wt %, or less than 0.1 wt % of a shape memory polymer composition.

In some embodiments, DMPA comprises about 0.1 wt % of a shape memory polymer composition. In other embodiments, DMPA comprises about 0.2 wt %, about 0.3 wt %, about 0.5 wt %, or about 0.75 wt % of a shape memory polymer composition.

A linear chain may be selected based on a requirement of a particular application, because of the ranges of rubbery moduli and recovery forces achieved by various compositions. In one embodiment, a SMP with a high recovery force and rubbery modulus may be made from a formulation with methyl-methacrylate (MMA) as the linear chain. In another embodiment, a SMP with a lower recovery force and rubbery modulus may be made from a formulation with tert-butyl acrylate (tBA) as the linear chain. In other embodiments, one or more other linear chains may be selected based on desired properties such as $T_g$, recovery force, and rubbery modulus.

In one embodiment, the copolymer network consists of two acrylate-based monomers. In one example of this embodiment, tert-butyl acrylate (tBA) may be crosslinked with poly (ethylene glycol) dimethacrylate (PEGDMA) via photopolymerization to form a cross-linked network. One subset of this formulation may consist of 20 wt % PEGDMA with a $M_n$=550 and 80 wt % tBA with 0.2-0.3 wt % photoinitiator (2,2 dimethoxy-2-phenylacetopenone (DMPA)). This exemplary polymer network has a glass transition temperature ($T_g$) of about 57° C. Another subset of this formulation may consist of 20 wt % PEGDMA with a $M_n$=1000 and 80 wt % tBA with 0.2-0.3 wt % DMPA. This exemplary polymer network has a $T_g$ of about 44° C.

In another embodiment, the copolymer network consists of three acrylate-based monomers. In one example of this embodiment, tBA and butyl acrylate (nBA) may be cross-linked with PEGDMA via photopolymerization to form a cross-linked network. One subset of this formulation may consist of 20 wt % PEGDMA with a $M_n$=550, 65 wt % tBA and 15 wt % nBA with 0.2-0.3 wt % DMPA. This exemplary polymer network has a $T_g$ of about 37° C. Another subset of this formulation may consist of 15 wt % PEGDMA with a $M_n$=550, 75 wt % tBA and 10 wt % nBA with 0.2-0.3 wt % DMPA. This exemplary polymer network has a $T_g$ of about 47° C.

The SMP material may be further varied to enhance desired properties. The SMP material may be photopolymerized from several different monomers and/or homopolymers to achieve a range of desired thermomechanical properties. A SMP formed from three or more monomers and/or homopolymers may achieve a range of rubbery modulus to glass transition temperatures, rather than a strictly linear relationship between these two thermomechanical properties. For example, tert-butyl acrylate may be substituted by 2-hydroxyethyl methacrylate or methyl methylacrylate to create either more hydrophilic or stronger networks, if desired. Additionally, if a hydrophilic monomer such as 2-hydroxyethyl methacrylate is substituted for tert-butyl acrylate, the SMP has the ability to swell post-implantation through hydrogel mechanisms.

Representative natural polymer blocks or polymers include proteins such as zein, modified zein, casein, gelatin, gluten, serum albumin, and collagen, and polysaccharides such as alginate, celluloses, dextrans, pullulane, and polyhyaluronic acid, as well as chitin, poly(3-hydroxyalkanoate)s, especially poly(.beta.-hydroxybutyrate), poly(3-hydroxyoctanoate) and poly(3-hydroxyfatty acids). Representative natural biodegradable polymer blocks or polymers include polysaccharides such as alginate, dextran, cellulose, collagen, and chemical derivatives thereof (substitutions, additions of chemical groups, for example, alkyl, alkylene, hydroxylations, oxidations, and other modifications routinely made by those skilled in the art), and proteins such as albumin, zein and copolymers and blends thereof, alone or in combination with synthetic polymers.

Representative synthetic polymer blocks or polymers include polyphosphazenes, poly(vinyl alcohols), polyamides, polyester amides, poly(amino acid)s, synthetic poly (amino acids), polyanhydrides, polycarbonates, polyacrylates, polyalkylenes, polyacrylamides, polyalkylene glycols, polyalkylene oxides, polyalkylene terephthalates, polyortho esters, polyvinyl ethers, polyvinyl esters, polyvinyl halides, polyvinylpyrrolidone, polyesters, polylactides, polyglycolides, polysiloxanes, polyurethanes and copolymers thereof. Examples of polyacrylates include poly(methyl methacrylate), polyethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate) and poly (octadecyl acrylate).

Synthetically modified natural polymers include cellulose derivatives such as alkyl celluloses, hydroxyalkyl celluloses, cellulose ethers, cellulose esters, nitrocelluloses, and chitosan. Examples of cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate and cellulose sulfate sodium salt. These are collectively referred to herein as "celluloses".

Representative synthetic degradable polymer segments include polyhydroxy acids, such as polylactides, polyglycolides and copolymers thereof; poly(ethylene terephthalate); polyanhydrides, poly(hydroxybutyric acid); poly(hydroxyvaleric acid); poly[lactide-co-(.epsilon.-caprolactone)]; poly[glycolide-co-(.epsilon.-caprolactone)]; polycarbonates, poly(pseudo amino acids); poly(amino acids); poly(hydroxyalkanoate)s; polyanhydrides; polyortho esters; and blends and copolymers thereof. Polymers containing labile bonds, such as polyanhydrides and polyesters, are well known for their hydrolytic reactivity. Hydrolytic degradation rates of these polymers may be altered by simple changes in the polymer backbone and the polymer's sequence structure.

Examples of non-biodegradable synthetic polymer segments include ethylene vinyl acetate, poly(meth)acrylic acid, polyamides, polyethylene, polypropylene, polystyrene, polyvinyl chloride, polyvinylphenol, and copolymers and mixtures thereof.

Hydrogels can be formed from polyethylene glycol, polyethylene oxide, polyvinyl alcohol, polyvinyl pyrrolidone, polyacrylates, poly (ethylene terephthalate), poly(vinyl acetate), and copolymers and blends thereof.

The polymers can be obtained from commercial sources such as Sigma Chemical Co., St. Louis, Mo.; Polysciences, Warrenton, Pa.; Aldrich Chemical Co., Milwaukee, Wis.;

Fluka, Ronkonkoma, N.Y.; and BioRad, Richmond, Calif. Alternately, the polymers can be synthesized from monomers obtained from commercial sources.

Various SMP properties may be controlled via variations in a cross-linker in the SMP formulation. A range of average molecular weights of cross-linker material for use in a SMP may be determined based upon the desired transition temperature, for example, a transition temperature close to human body temperature. The transition temperature affects the range of possible average molecular weights of cross-linker material that may be used in the SMP because certain combinations of average molecular weights and of percentage weights of cross-linker produce certain transition temperatures and other combinations produce other transition temperatures. Varying the molecular weight of the cross-linker may also alter hydrophobicity and/or hydrophylicity of a shape memory polymer composition, which may allow better integration with medical fabrics or meshes that are generally more hydrophobic or hydrophilic.

The molecular weight of a cross-linker, for example PEGDMA, in a shape memory polymer composition may be from about $M_n=500$ to about $M_n=2000$. In some embodiments, PEGDMA has a $M_n$ less than 2000. In some embodiments, PEGDMA has a $M_n$ less than 1500. In other embodiments, PEGDMA has a $M_n$ less than 1000. In still other embodiments, PEGDMA has a $M_n$ less than 750.

In some embodiments, PEGDMA has a $M_n$ greater than 500. In some embodiments, PEGDMA has a $M_n$ greater than 750. In other embodiments, PEGDMA has a $M_n$ greater than 1000. In still other embodiments, PEGDMA has a $M_n$ greater than 1500.

In some embodiments, PEGDMA has a $M_n=500$. In some embodiments, PEGDMA has a $M_n=550$. In other embodiments, PEGDMA has a $M_n$, $=750$. In other embodiments, PEGDMA has a $M_n=1000$. In still other embodiments, PEGDMA has a $M_n=1500$. In some embodiments, PEGDMA has a $M_n=2000$.

A range of percentage weights of cross-linker material for use in a SMP is also determined from the selected transition temperature. Certain combinations of average molecular weights of cross-linker and percentage weights of cross-linker may be used in the SMP formulation to achieve a certain transition temperature. Determining the range of percentage weight cross-linker and the range of molecular weights may be performed based upon a relationship between transition temperature, molecular weight, and percentage weight cross-linker. The relationship is specific to the linear chain and cross-linker used. Other inputs or manufacturing techniques may also affect the relationship and eventual transition temperature of a SMP.

In one embodiment, empirically-derived relationships which relate molecular weight and weight percentage cross-linker to (a) the transition temperature, (b) the rubbery modulus, and/or (c) a recovery time characteristic may be used. The range of rubbery moduli is determined by evaluating the relationship between rubbery modulus, percentage weight of cross-linker, and molecular weights for a number of combinations determined. This results in a range of possible rubbery moduli for SMPs that also has the desired transition temperature. In another embodiment, relationships may be derived from known theoretical models.

A rubbery modulus is selected from a range of rubbery moduli as an initial goal value of rubbery modulus for the SMP. The modulus selection may alternatively be performed after a transition temperature is selected, which produces another range of rubbery moduli. In other words, the method may be performed iteratively, repeatedly, and/or in parts. The molecular weight and percentage weight of cross-linker is determined based on the selected rubbery modulus by using the relationship between rubbery modulus, molecular weight and percentage weight of cross-linker to find the combination of molecular weight and percentage weight that corresponds to the rubbery modulus selected.

In another embodiment, determining a range of molecular weights and percentage weights of cross-linker may be performed by creating and/or selecting a table, graph, or chart corresponding to a desired transition temperature or a desired rubbery modulus among a plurality of tables, graphs, and/or charts. In this embodiment, the tables, graphs, and/or charts include information from the relationships described above and outline ranges of molecular weights and percentage weights cross-linker that correspond to the desired value of the property (e.g., transition temperature).

A cross-linker, for example PEGDMA, of any molecular weight or any range of molecular weights may comprise from about 1 wt % to about 30 wt % of a shape memory polymer composition. In some embodiments, PEGDMA comprises more than 1 wt % of a shape memory polymer composition. In other embodiments, PEGDMA comprises more than 5 wt %, more than 10 wt %, more than 15 wt %, more than 20 wt %, or more than 25 wt of a shape memory polymer composition.

In some embodiments, PEGDMA comprises less than 30 wt % of a shape memory polymer composition. In other embodiments, PEGDMA comprises less than 25 wt %, less than 20 wt %, less than 15 wt %, less than 10 wt %, or less than 5 wt % of a shape memory polymer composition.

In some embodiments, PEGDMA comprises about 1 wt % of a shape memory polymer composition. In other embodiments, PEGDMA comprises about 2 wt %, about 10 wt %, about 15 wt %, about 18 wt %, about 19 wt %, about 20 wt %, about 22 wt %, or about 23 wt % of a shape memory polymer composition.

In some implementations, the shape memory polymer may comprise thiol and/or vinyl monomers or oligomers. In some implementations, monomers or oligomers with acrylate or methacrylate functional groups may be combined with thiol and/or vinyl monomers or oligomers.

A thiol-vinyl SMP system includes molecules containing one or more thiol functional groups, which terminate with —SH, and molecules containing one or more vinyl functional groups, which contain one or more carbon-carbon double bonds. The vinyl functional groups in the system may be provided by, for example, allyl ethers, vinyl ethers, norborenes, acrylates, methacrylates, acrylamides or other monomers containing vinyl groups. In some implementations, additional fillers, molecules, and functional groups may be provided to tailor and provide additional properties. In different embodiments, the thiol-ene system has about 1-90% of its functional groups as thiol functional groups or 2%-65% thiol functional groups. The balance of the functional groups (35% to 98% of the functional groups may be vinyl functional groups. In an embodiment, 5-60 mol % of the functional groups in the system may be thiol functional groups and 95-40 mol % vinyl functional groups. In some exemplary embodiments, the system of molecules containing thiol functional groups and the molecules forming vinyl functional groups is capable of forming a network.

In one class of thiol-vinyl systems, the vinyl monomer is not readily homopolymerizable and is termed an ene monomer. In these systems, the polymerization proceeds via a radically initiated step growth reaction between multifunctional thiol and ene monomers. The reaction proceeds sequentially, via propagation of a thiyl radical through a vinyl functional group. This reaction is followed by a chain transfer of a hydrogen radical from the thiol which regenerates the thiyl radical. the process then cycles many times for each radical generated in the photoinitiation step. This successive propagation/chain transfer mechanism is the basis for thiol-ene polymerization.

The monomer or oligomer comprising a vinyl group may further comprise at least one urethane group. In an embodiment, the monomer comprises from 2-4 or 2-6 urethane groups. In an embodiment, the oligomer comprises from 4-40 urethane groups. A monomer comprising urethane groups may be formed by reacting a polyisocyanate with a molecule comprising an alcohol group and at least two vinyl groups. For example, a diisocyanate could be reacted with a trimethylolpropane diallyl ether or allyl pentaerythritol.

A urethane acrylate (for example Ebecryl-8411) may comprise from about 0 wt % to about 10 wt % of a shape memory polymer composition. In some embodiments, urethane acrylate comprises more than 0 wt % of a shape memory polymer composition. In other embodiments, urethane acrylate comprises more than 2 wt %, more than 4 wt %, more than 6 wt %, or more than 8 wt % of a shape memory polymer composition.

In some embodiments, urethane acrylate comprises less than 10 wt % of a shape memory polymer composition. In other embodiments, urethane acrylate comprises less than 8 wt %, less than 6 wt %, less than 4 wt %, or less than 2 wt % of a shape memory polymer composition.

In some embodiments, urethane acrylate comprises about 0 wt % of a shape memory polymer composition. In other embodiments, urethane acrylate comprises about 2 wt %, about 3.5 wt %, about 5 wt %, or about 7.5 wt % of a shape memory polymer composition.

SMP-Integrated Fabrics

For a discussion of medical fabrics that may utilize a SMP as discussed above, reference is now made to FIGS. 1A-2D which illustrate various embodiments of a SMP-integrated fabric and apparatus for making the same.

Figure 1C:
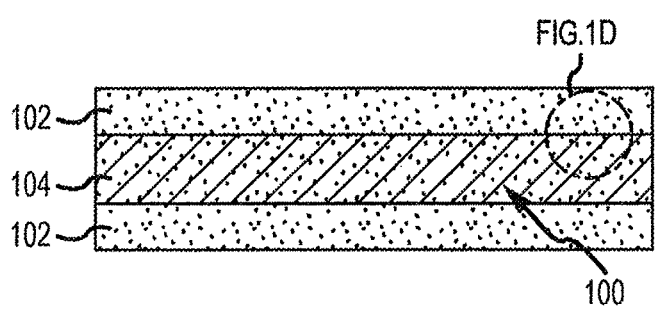
FIG. 1C is a schematic side elevation view of a SMP-integrated fabric formed by the mold set-up of FIG. 1A.
Figure 1D:
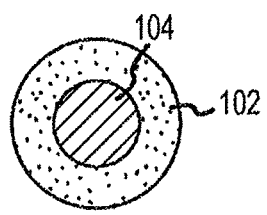
FIG. 1D is a schematic enlarged, cross-section view of a strand of SMP-integrated fabric formed by the mold set-up of FIG. 1A.

FIGS. 1A-1D depict a first exemplary implementation of a SMP-integrated fabric 100 and an exemplary apparatus for forming the same. As depicted in FIG. 1A, a medical fabric 104 is held at its ends 104a,104b with a molding gasket 106 and is further coated on each side with a shape memory polymer 102. Because the medical fabric 104 is formed by the interconnection of woven fibers, the medical fabric 104 is by nature porous, thus allowing the shape memory polymer 102 to integrate with the medical fabric 104 and coat each individual thread or strand making up the medical fabric 104. Such coating is depicted in FIG. 1D where the shape memory polymer 102 is depicted as completely surrounding an individual strand of the medical fabric 104. Returning to FIG. 1A, a plate of glass 108 (e.g., a glass slide) may be placed on each side of the coated medical fabric 104 and supported and separated by the molding gaskets 106. The glass plate 108 retains the shape memory polymer 102 about the medical fabric 104 in a thin layer for the curing (polymerization) process. Alternatively, the mold includes glass faces that create a space into which the medical fabric is placed and into which the SMP is injected (not shown).

The molding apparatus 112 (e.g. the glass 108, the molding gaskets 106 and the material found therebetween (e.g. the SMP 102 disposed about the medical fabric 104)) is then exposed to ultraviolet light which passes through each of the glass plates to cure the shape memory polymer 102, thus binding it around the strands of the medical fabric 104 to create the SMP-integrated fabric 100.

Figure 3C:
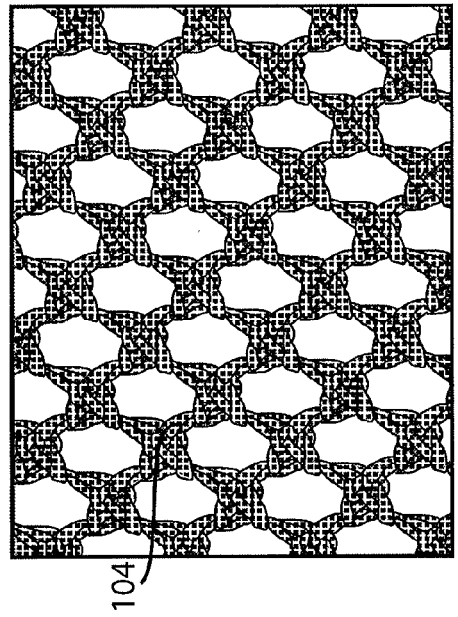
FIG. 3C is a schematic diagram of an SMP-integrated medical fabric of FIG. 1B in which the medical fabric is fully encapsulated by the SMP.
Figure 3A:
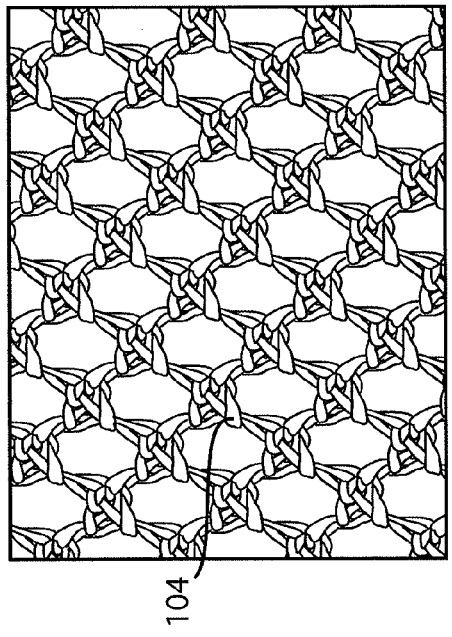
FIG. 3A is a schematic diagram of a medical mesh fabric without the addition of an SMP.

As shown in FIGS. 1D and 1C, the shape memory polymer 102 both presents as a coating on each side of the medical fabric 104 and integrates through the weave of the medical fabric 104, for example, by fully coating each individual thread or strand of the medical fabric 104. Depending on the thickness of the threads of strands that make up the medical fabric 104 and the tightness of the weave of the medical fabric 104, the nature of the integration of the shape memory polymer 102 with the medical fabric 104 may differ between the materials. For example, more tightly woven materials with a smaller pore between strands of the medical fabric 104 may limit the ability of the shape memory polymer 102 to fully coat the individual strands but instead present more as a top coating on each side of or an encapsulation of the medical fabric (see FIG. 3C). Alternatively, medical fabric 104 that is less tightly woven allows the shape memory polymer 102 to completely coat (or almost completely coat) or integrate with the individual strands of the medical fabric 104 (see FIG. 3B), which allows for the retention of porosity between the strands of the medical fabric 104.

Figure 2A:
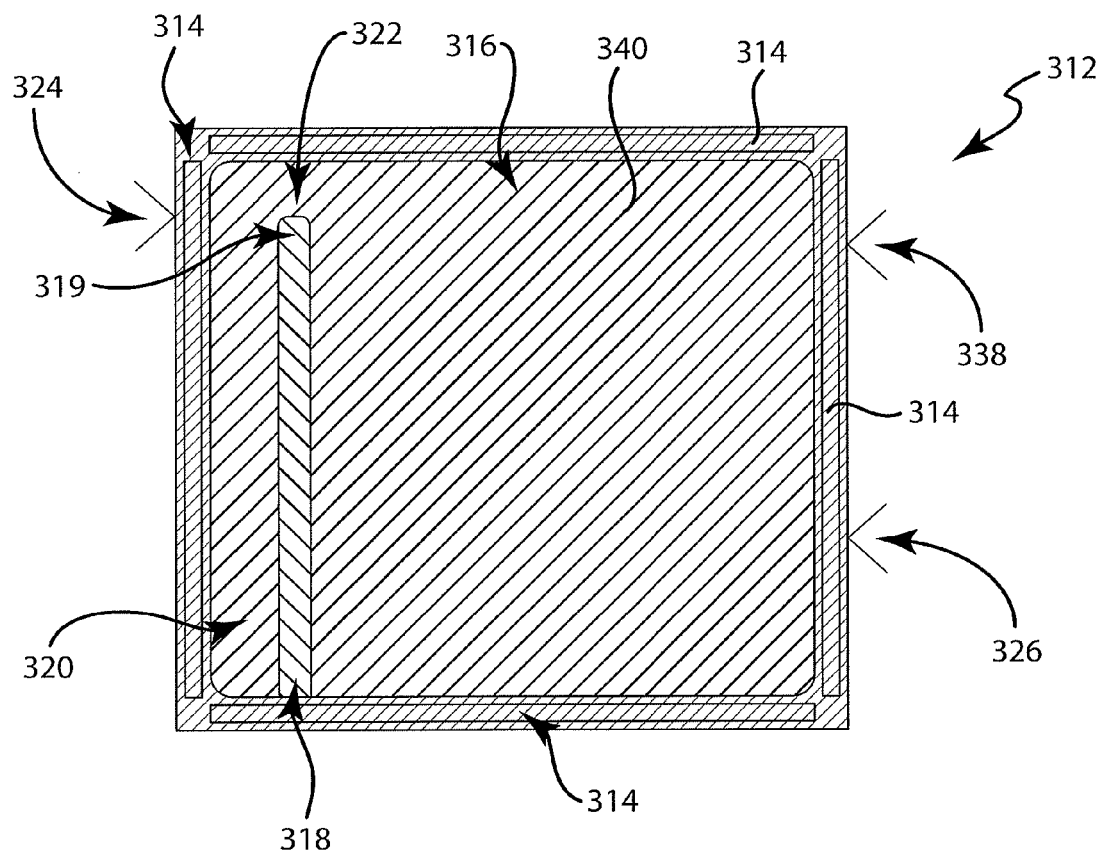
FIG. 2A is a schematic top plan view of another exemplary implementation of a mold set-up for curing a SMP-integrated fabric.
Figure 2B:
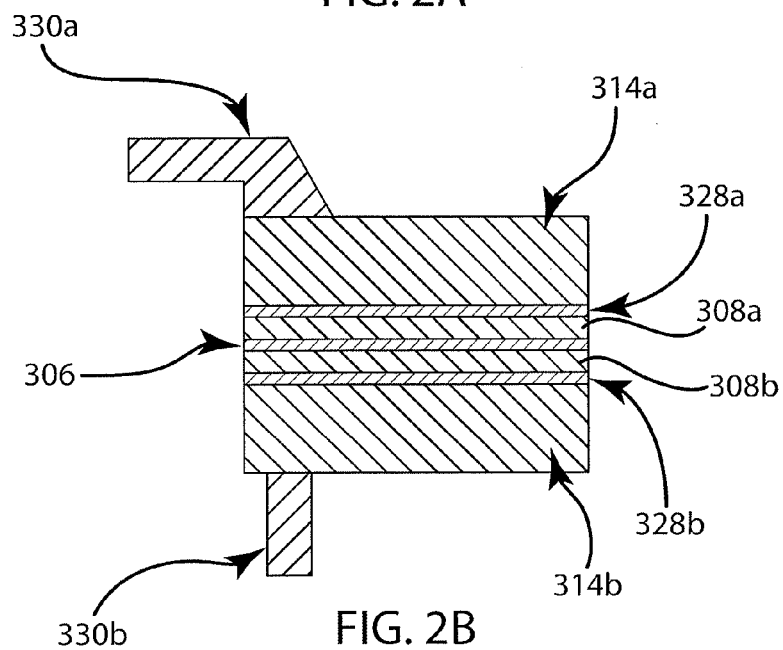
FIG. 2B is a schematic side cross-section view of a portion of the mold of FIG. 2A.
Figure 2C:
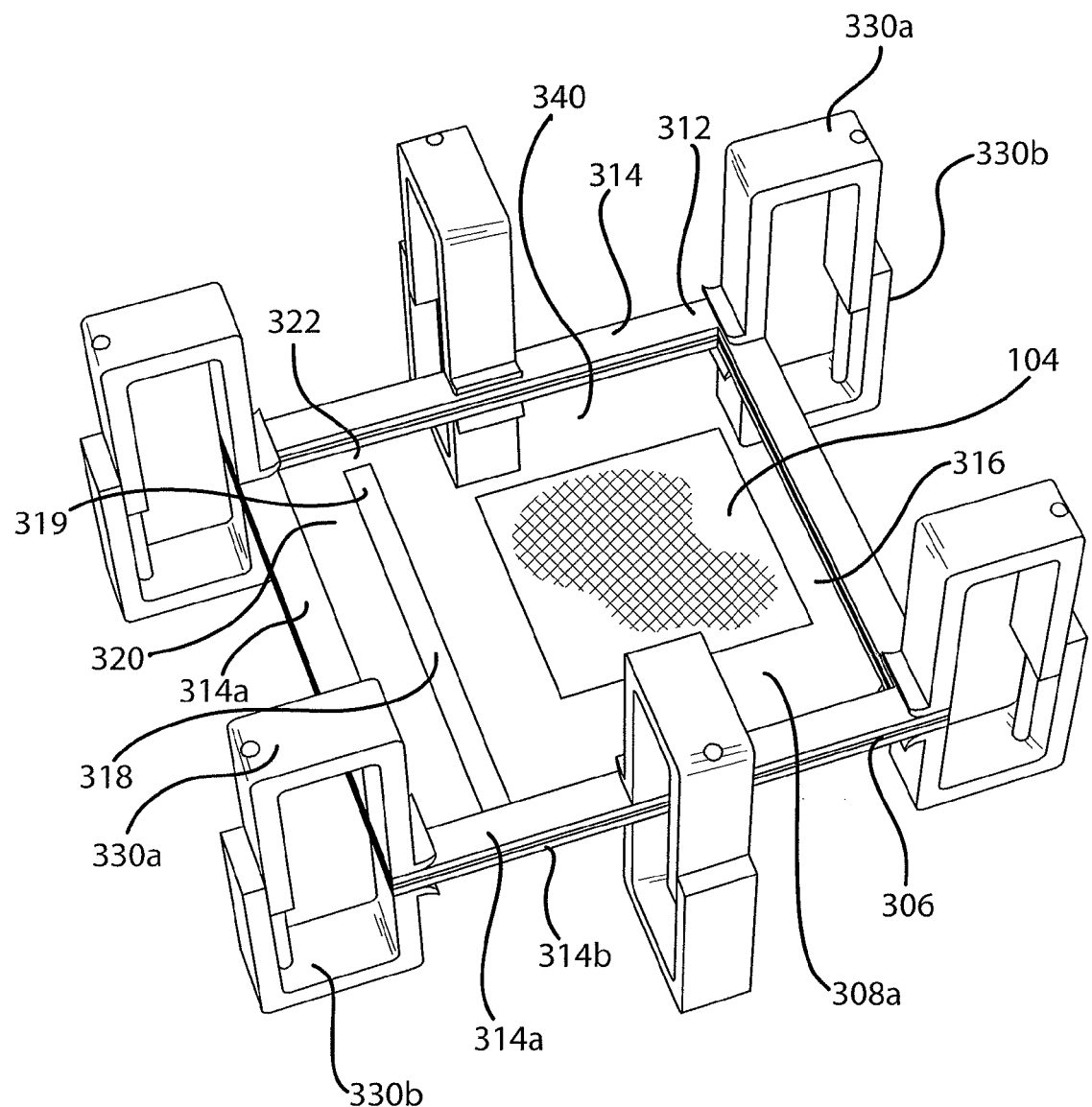
FIG. 2C is a schematic top isometric view of the mold of FIG. 2A.

FIGS. 2A-2C depict another exemplary apparatus 312 for forming a SMP-integrated fabric. As depicted in FIG. 2A, a rectangular plastic frame 314 surrounds a rectangular frame area 340. The frame 314 may be constructed of any plastic, such as a thermoplastic polymer, for example polyoxymethylene (e.g., Celcon®, Delrin®, Duracon®, or Hostaform®). A well gasket 318 is positioned proximate to one edge of the frame 314 and is separated from the frame 314 by a well 320. An overflow inlet 322 connects a polymerization zone 316 to the well 320 by transversing the distal end 319 of the well gasket 318. The apparatus 312 also includes an inlet 338 for flowing SMP into the apparatus, a gas inlet 324 for injection of gas into the apparatus, and a gas outlet 326 for allowing gas to exit the apparatus 312.

As shown in FIG. 2B, the frame 314 comprises an upper frame 314a and a lower frame 314b. The upper and lower frames 314a, 314b sandwich one or more layers of cushion 328, glass 308, and/or molding gaskets 306. For example, in the depicted embodiment, the upper and lower frames 314a, 314b sandwich an upper and a lower cushion layer 328a, 328b, which sandwich an upper and a lower glass plate 308a, 308b, which sandwich a molding gasket 306. The upper and lower frames 314a, 314b are secured together by at least one removable clamp 330 having an upper clamp portion 330a and lower clamp portion 330b.

When the apparatus 312 is assembled, as shown in FIG. 2C, a medical fabric 104 is positioned in the polymerization zone 316 and between the upper and lower glass plates 308a, 308b. The frame 314 is captured between and secured by the upper and lower clamp portions 330a, 330b. In the embodiment depicted in FIG. 2C, six clamps 330 are used, but any number of clamps 330 may be employed.

In an exemplary method of using the apparatus 312 of FIG. 2A-2C, the apparatus 312 is purged with an inert gas, such as nitrogen or argon gas, by injecting the gas into the gas inlet 324 and allowing gas to escape from the gas outlet 326. After the apparatus 312 has been purged of air by the inert gas, the gas inlet 324 and gas outlet 326 may be closed. Alternatively, the gas inlet 324 and gas outlet 326 may be left open, and the inert gas may be allowed to flow through the apparatus 312 during the curing process.

SMP is injected through the SMP inlet 338. The apparatus 312 is gently shaken or tilted, either manually or mechanically, to coat the medical fabric 104 with SMP. Excess SMP accumulates in the SMP well 320. The upper and lower glass plates 308a, 308b retain the SMP about the medical fabric 104 in a thin layer for the curing process.

Figure 2D:
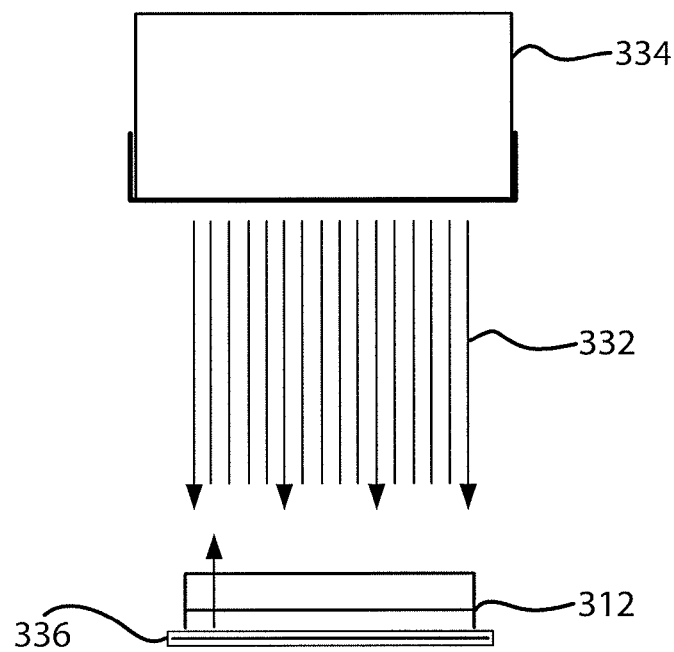
FIG. 2D is a schematic diagram of the mold of FIG. 2A exposed to ultraviolet light.

In one implementation, the apparatus 312 is then exposed to ultraviolet light 332 as depicted in FIG. 2D. The ultraviolet light 332 passes through each of the glass plates 308a, 308b to cure the SMP, thus binding it around strands of the medical fabric 104 to create a SMP-integrated fabric. The apparatus 312 is positioned a set distance from an ultraviolet light source 334 in order to obtain desired ultraviolet light intensities at various positions above, within, and below the apparatus 312. For example, an ultraviolet light source 334 emitting approximately 117 mW/cm$^2$ may be positioned above the apparatus 312 such that the top surface of the apparatus 312 receives approximately 21 mW/cm$^2$ and the bottom surface receives approximately 18 mW/cm$^2$. A mirror 336 may be placed under the bottom surface of the apparatus 312 to reflect light back to the apparatus 312, including back to the medical fabric 104, at an intensity of approximately 9-10 mW/cm$^2$. However, desired intensities may be changed based on a variety of factors including composition of the SMP and application for the SMP-integrated fabric that is produced. Duration and timing of ultraviolet light exposure may also depend on the composition of the SMP and the application for the resulting SMP-integrated fabric.

The ultraviolet light 332 also cures excess SMP in the SMP well 320 to produce cured SMP samples. The cured SMP samples can be used for testing.

Figure 2E:
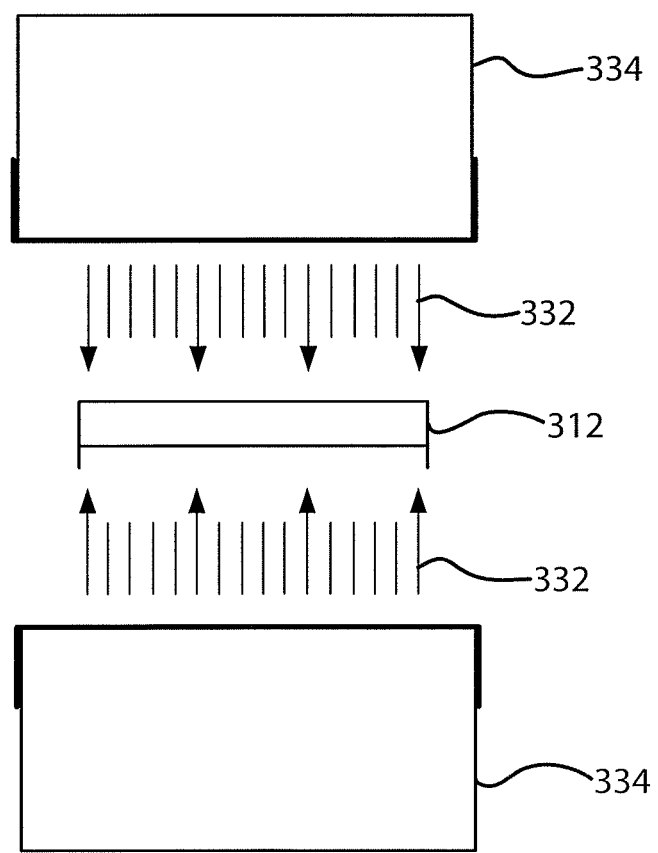
FIG. 2E is a schematic diagram of the mold of FIG. 2A exposed to ultraviolet light.

In another implementation, the apparatus 312 is exposed to ultraviolet light 332 as depicted in FIG. 2E. An ultraviolet light source 334 is positioned both above and below the apparatus to cure the SMP from above and below.

The apparatus 312 of FIGS. 2A-2D may be used to create porous or non-porous SMP-integrated fabrics as described in more detail in Example 9.

In all of the embodiments depicted in FIGS. 1A-3C, once the SMP-integrated fabrics are formed as desired, they may be mechanically deformed for storage or for a more suitable configuration for delivery in vivo. For example, the SMP-integrated medical fabrics once formed may be rolled up for delivery through a catheter or a lumen of an endoscope or other instrument. The SMP-integrated medical fabrics may be deployed from the delivery device. Then, upon being subject to an external stimulus, for example, body temperature, the SMP-integrated fabric may unfurl from its rolled configuration and return to its original memory configuration for use by a clinician in a particular procedure for which the SMP-integrated fabric was developed.

In one implementation, SMP-integrated fabrics may be formed as hernia patches. The shape memory polymer portion of a SMP hernia patch may be fabricated in varying thicknesses with the minimum thickness determined by the thickness of the traditional patch fabric (e.g., polyester (polyethylene terephthalate), Dacron®, polytetrafluoroethylene (PTFE or Gore-Tex®), expanded polytetrafluoroethylene (ePTFE), polypropylene, polypropylene derivatives, and combinations thereof) and up to almost any thickness. The polypropylene mesh has a coarse weave and is woven of strands of polypropylene. An SMP-integrated polypropylene hernia patch remains quite porous while fully coating all the polypropylene strands with the shape memory polymer. PTFE fabric (e.g. Gore-Tex®) is soft and can be rolled into any shape, but cannot unfurl itself. In contrast, a SMP-integrated PTFE patch can hold the rolled shape of the PTFE fabric and self deploy after the activation time and/or temperature has been reached. Similar performance characteristics may be achieved with the SMP-integrated Dacron® patches. Also, the SMP-integrated Dacron® patch is able to achieve the thinnest patch out of the three clinical patch materials at 0.0135 inches thick. The ability to maintain material thickness of the standard patch fabric, even with the SMP co-polymerization, allows the SMP hernia patch to be used with existing insertion devices. SMP hernia patches may also be steam sterilized without loss of shape memory functionality. A SMP hernia patch, or any SMP-integrated medical fabric, may be constrained in a desired configuration during sterilization.

Integration of the SMP with the traditional medical fabrics does not alter the shape memory functionality of the SMP. This indicates that all of the design tools for controlling activation rate for traditional SMP materials apply to SMP hernia patches. A clinically relevant example of this is the ability to control the activation time, or the time that must elapse before the SMP hernia patch will begin to self deploy. For complicated procedures, the activation time may be set to a large value giving the surgeon ample time to place the patch before it self deploys, or for simple surgeries, the activation time may be set low so as to speed up the time to self-deployment.

The shape of the SMP hernia patch has no impact on incorporation of the shape memory polymer or its functionality. That is, the SMP hernia patch is self-deploying, which makes placing the patch easier for the surgeon and reduces surgical time substantially. SMP hernia patches have successfully demonstrated the ability to maintain their packaged shape in repeated fashion. In contrast, commercially available hernia patches exhibit creep, inability to maintain a particular pre-defined shape after deployment, and an inability to deploy on command with the application of thermal energy (e.g., body temperature). SMP hernia patches can also be programmed through proper formulation of the shape memory polymer to activate after precise periods of time have elapsed. Activation and deployment are discussed in more detail below (see, e.g., Examples 6 and 7 and FIGS. 7, 8A and 8B).

EXAMPLES

The following examples illustrate various aspects of the disclosure and should not be considered limiting.

Example 1—Preparation of Shape Memory Polymer (SMP)-Integrated Fabrics

Chemicals tert-butyl acrylate (tBA), butyl acrylate (nBA) and poly(ethylene glycol) dimethacrylate (PEGDMA) with an average molecular weight of $M_n$=1000 (PolySciences) or $M_n$=550, and 2,2-dimethoxy-2-phenylacetophenone (DMPA) photo-initiator were obtained from Sigma-Aldrich, unless otherwise noted. Four polymer solutions were prepared by combining tBA, nBA, and PEGDMA, as shown in Table 1, and 0.2-0.3 wt % DMPA photo-initiator.

TABLE 1

|  | tBA (wt %) | nBA (wt %) | PEGDMA (wt %) |
| --- | --- | --- | --- |
| Formula A | 80 | 0 | 20 ($M_n$ = 550) |
| Formula B | 65 | 15 | 20 ($M_n$ = 550) |
| Formula C | 75 | 10 | 15 ($M_n$ = 550) |
| Formula D | 80 | 0 | 20 ($M_n$ = 1000) |

SMP solution was applied to commercially available polyester surgical meshes (PETKM14001, Textile Development Associates) using a free radical UV-polymerization process. Surgical meshes were placed in glass molds (75 mm×25 mm) in a flat configuration, and SMP solution was injected. Glass molds were placed under a 365 nm UV lamp (Model B100AP; Black-Ray) for 10 minutes for photo-curing.

Example 2—Dynamic Mechanical Analysis of SMP-Integrated Fabrics

Dynamic Mechanical Analysis (DMA) was performed in tensile loading to determine glass transition temperature ($T_g$) and storage modulus of the SMP formulations described in Table 1. DMA was performed using a TA Q800 DMA, after cutting a sample of each SMP formula into strips approximately 24 mm×4 mm×1 mm. The samples were thermally equilibrated at 0° C. for 5 minutes and then heated to 100° C. at a rate of 3° C. per minute. Testing was performed in cyclic strain control at 0.1% strain and at a frequency of 1.0 Hz. A preload force of 0.01N and a force track setting of 125% were used.

Figure 5:
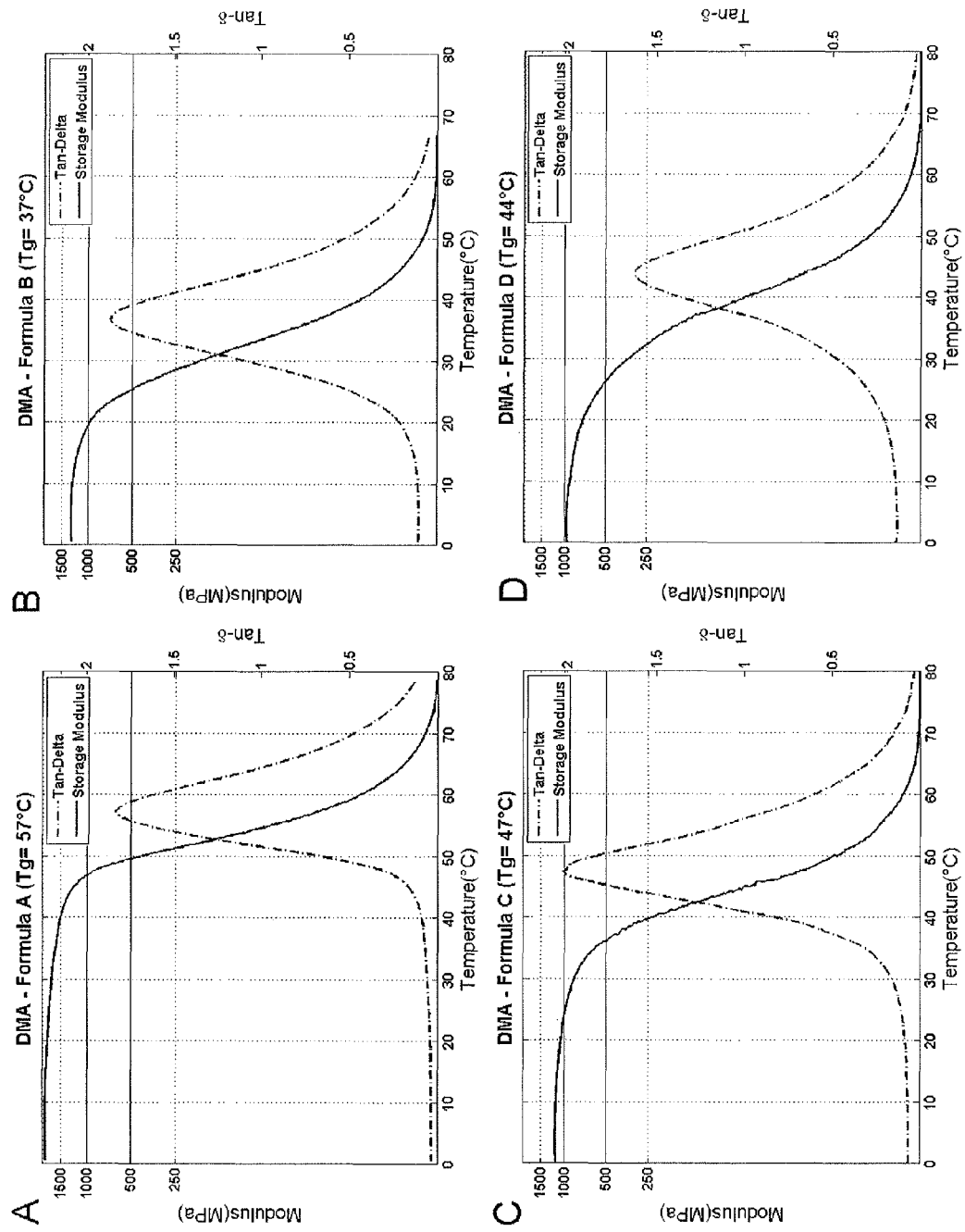
FIG. 5 is a graph of dynamic mechanical analysis testing of the four SMP-formulations of Table 1.

A sample of each SMP formula was characterized by storage modulus and the tan delta curve. The $T_g$ was determined to be the peak of the tan delta curve. Results are presented in FIG. 5. The storage modulus of Formula A ranged from 1528.5 MPa to 3.6 MPa, Formula B ranged from 1298.1 MPa to 4.1 MPa, Formula C ranged from 1176.7 MPa to 2.7 MPa, and Formula D ranged from 970.7 MPa to 2.3 MPa. The $T_g$ of Formula A was found to be 57° C., Formula B was found to be 37° C., Formula C was found to be 47° C., and Formula D was found to be 44° C.

Example 3—Uniaxial Tensile Tests of SMP-Integrated Fabrics

Uniaxial tensile tests were performed on the SMP formulations described in Table 1, and were based upon ASTM Test Method D638-03, using Type V specimen geometry. Specimens measuring approximately 9.5 mm×63.5 mm×1 mm were cut using a D638-03 Type-V cast steel die (North East Cutting Die Corp., Portsmouth, N.H.). Tensile tests were performed using an Insight 5SL test machine (MTS, Eden Prairie, Minn.), in an aqueous environmental chamber at 37° C. with the specimen immersed in deionized water, using a tension rate of 5 mm/min.

Uniaxial tensile tests were performed to characterize the tensile strength of SMP formulas alone, unmodified mesh materials alone, and SMP-integrated mesh materials. Tensile test results are shown in Table 2, with sample size denoted "n."

TABLE 2

|  |  | Tg (° C.) | Tensile Strength (N) | Strain to Failure (mm) | n |
|---|---|---|---|---|---|
| Control | PET mesh alone | — | 16.65 ± 3.30 | 21.92 ± 3.76 | 14 |
| Formula A | SMP alone | 57° | 15.96 ± 1.09 | 28.59 ± 3.78 | 6 |
|  | SMP + Mesh | — | 28.10 ± 3.42 | 17.82 ± 1.25 | 6 |
| Formula B | SMP alone | 37° | 3.96 ± 0.25 | 10.07 ± 0.57 | 9 |
|  | SMP + Mesh | — | 19.62 ± 0.36 | 17.55 ± 1.46 | 6 |
| Formula C | SMP alone | 47° | 5.75 ± 0.73 | 18.85 ± 1.50 | 10 |
|  | SMP + Mesh | — | 22.50 ± 2.47 | 17.38 ± 1.85 | 6 |
| Formula D | SMP alone | 44° | 7.15 ± 0.77 | 31.85 ± 3.69 | 7 |
|  | SMP + Mesh | — | 17.45 ± 2.82 | 17.45 ± 3.35 | 6 |

Example 4—Strain-to-Failure Comparison of SMP Alone to Control Mesh

Figure 6A:
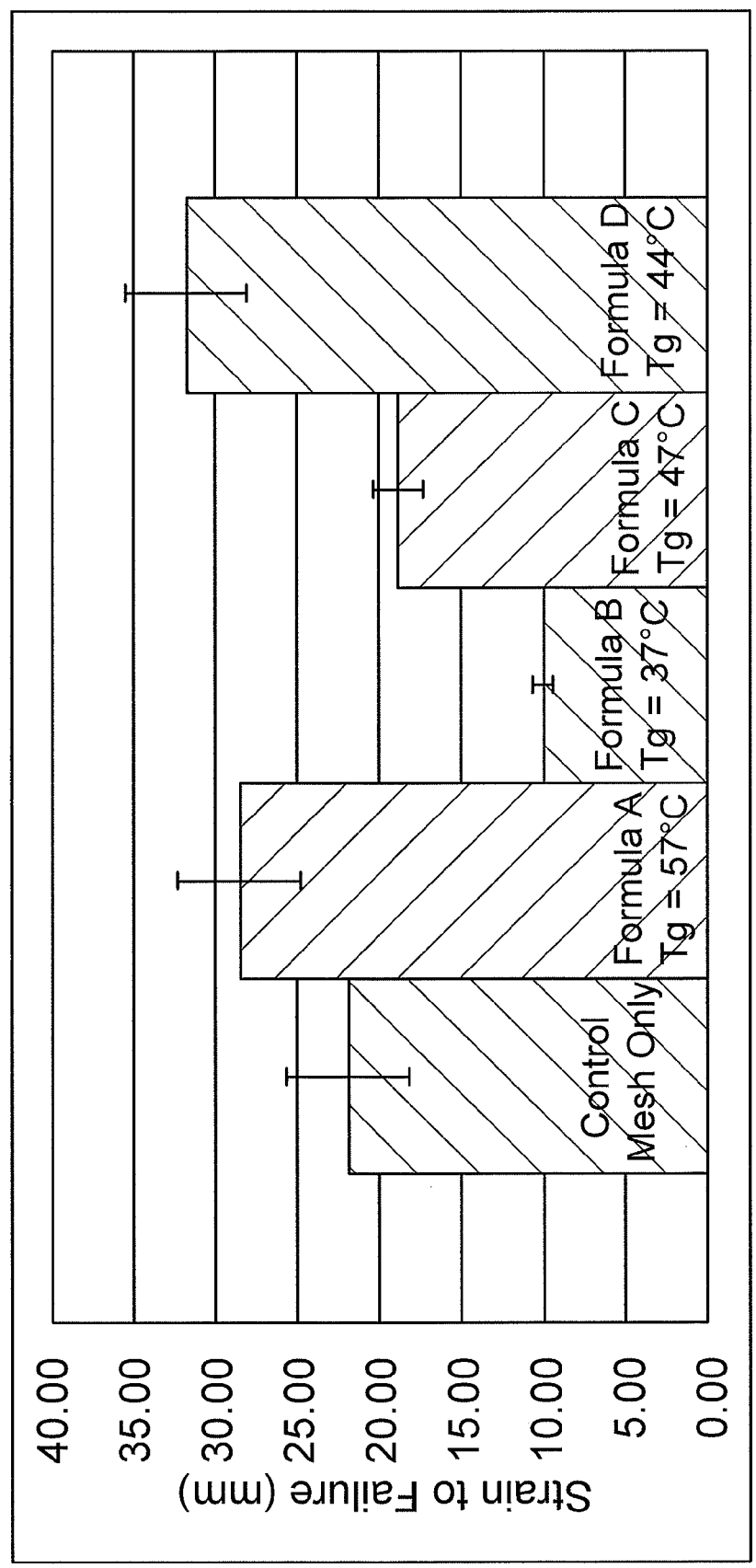
FIG. 6A is a graph of the strain-to-failure results of the SMP formulations from Table 2.

The results of Example 3 revealed that, at high strain, the SMP-integrated mesh behaved more like the control sample, in that SMP began separating from the mesh and mesh fibers engaged similar to that of the tensile test of the unmodified mesh. For this reason, SMP alone was tested to ensure maximization of strain-to-failure. The strain-to-failure of the SMP formulations alone are shown in FIG. 6A.

Figure 6B:
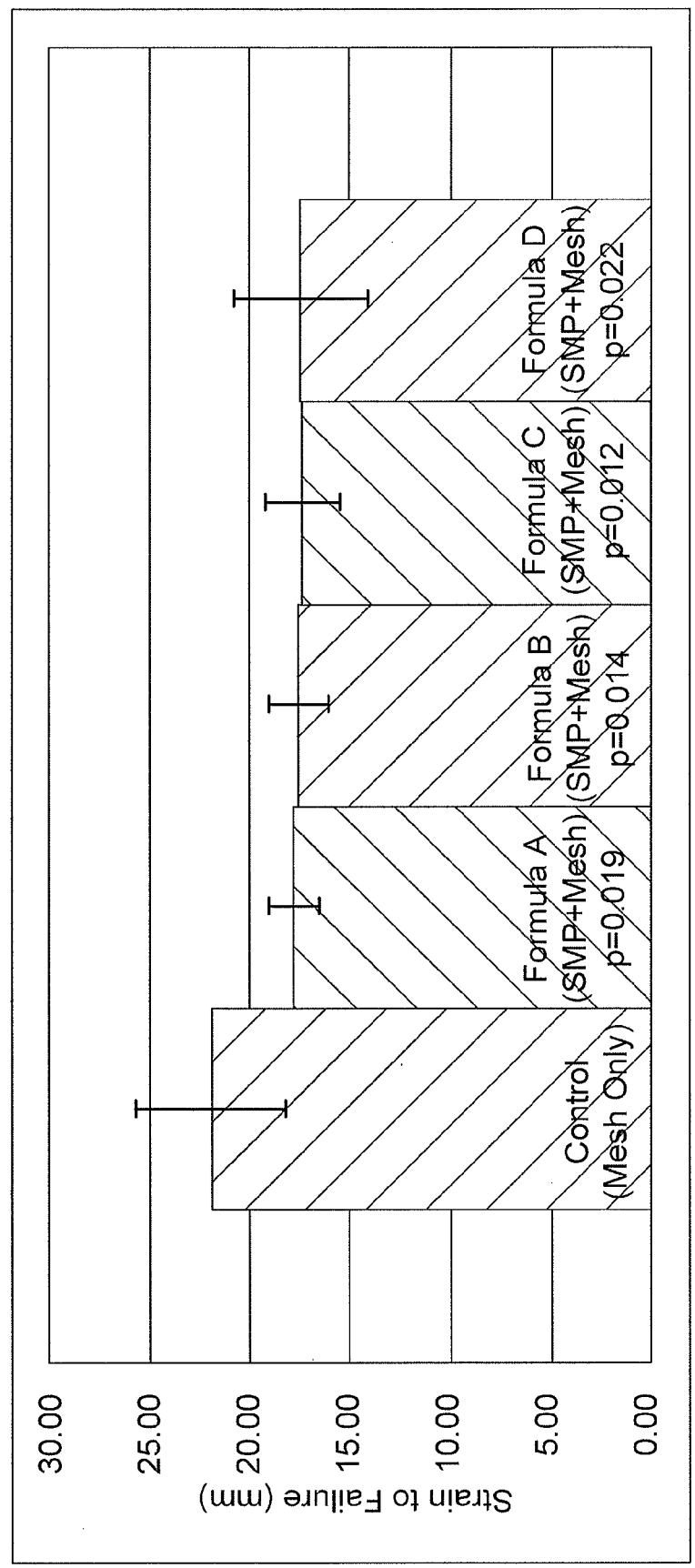
FIG. 6B is a graph of the strain-to-failure results of the SMP-integrated meshes from Table 2.

It was observed that higher strain-to-failure reduced the separation between SMP and mesh. Combining lower tensile strength and higher strain-to-failure in SMP-integrated meshes suggests the SMP has less impact on the mechanical strength of the mesh itself, allowing deformation to occur in a similar manner to that of unmodified mesh. A Student's T-test was used to compare strain-to-failure of the control (mesh alone) and each SMP-integrated mesh. No statistical difference between strain-to-failure of the control and SMP-integrated mesh was observed, as shown in FIG. 6B.

Example 5—Comparison of SMP-Integrated Fabrics

The $T_g$ and strain-to-failure of each of the SMP-integrated fabrics of Example 1 were compared. Formula A was comprised of 20% PEGDMA-550, 80% tBA, and no nBA, and had a $T_g$ of 57° C. Without being limited to any mechanism or mode of action, at 37° C. the stiffness of this formula likely caused an increase in the tensile strength and reduction of strain-to-failure of the SMP-integrated mesh compared to the control mesh itself. Thus, a $T_g$ of 57° C. was determined to be too high, and improvements upon Formula A were required.

Formula B was comprised of 20% PEGDMA-550, 65% tBA, and 15% nBA, and had a $T_g$ of 37° C. Without being limited to any mechanism or mode of action, the addition of nBA appeared to lower the Formula B $T_g$ compared to Formula A. But Formula B showed poor performance with a 65% reduction in strain-to-failure compared to Formula A.

Formula C was comprised of 15% PEGDMA-550, 75% tBA, and 10% nBA. The $T_g$ was 47° C. and strain-to-failure increased 47% over Formula B. Without being limited to any mechanism or mode of action, the lower weight percentage of PEGDMA-550 likely reduced the effective amount of cross-linking in the copolymer, allowing for the higher strain observed.

In Formula D, longer PEGDMA chains were introduced by using 20% PEGDMA-1000, which likely further reduced the effective amount of cross-linking in the copolymer while increasing the maximum achievable strain compared to Formula C. Formula D also included 80% tBA. Formula D resulted in a $T_g$ of 44° C. and improved strain-to-failure over Formula C at a relatively low tensile strength.

Example 6—Time to Unroll in Water Testing of SMP-Integrated Fabrics

The time required for SMP-integrated meshes to unroll was evaluated to determine the impact of adding shape memory polymer as a function of temperature. SMP-integrated mesh specimens approximately 75 mm×25 mm were prepared as has been described in the art (e.g., Yakacki et al, *Biomaterials*, vol. 28, no. 14, pp. 2255-2263, April 2007; Yakacki et al, *Biomed. Materials*, vol. 3, no. 1, February 2008; Gall et al, *J. Biomed. Materials Res. Pt. A*, vol. 73A, no. 3, pp. 339-348, May 2005). Each specimen was heated using hot water (>65° C.) to bring the sample into the rubbery region. The sample was rolled tightly by hand and cooled using cold water (<7° C.) to bring the sample into the glassy region to retain the rolled configuration. Using soft tipped forceps, each rolled mesh formula was placed individually into a deionized water bath held at approximately 37° C. to simulate introduction into a wet surgical environment.

Figure 7:
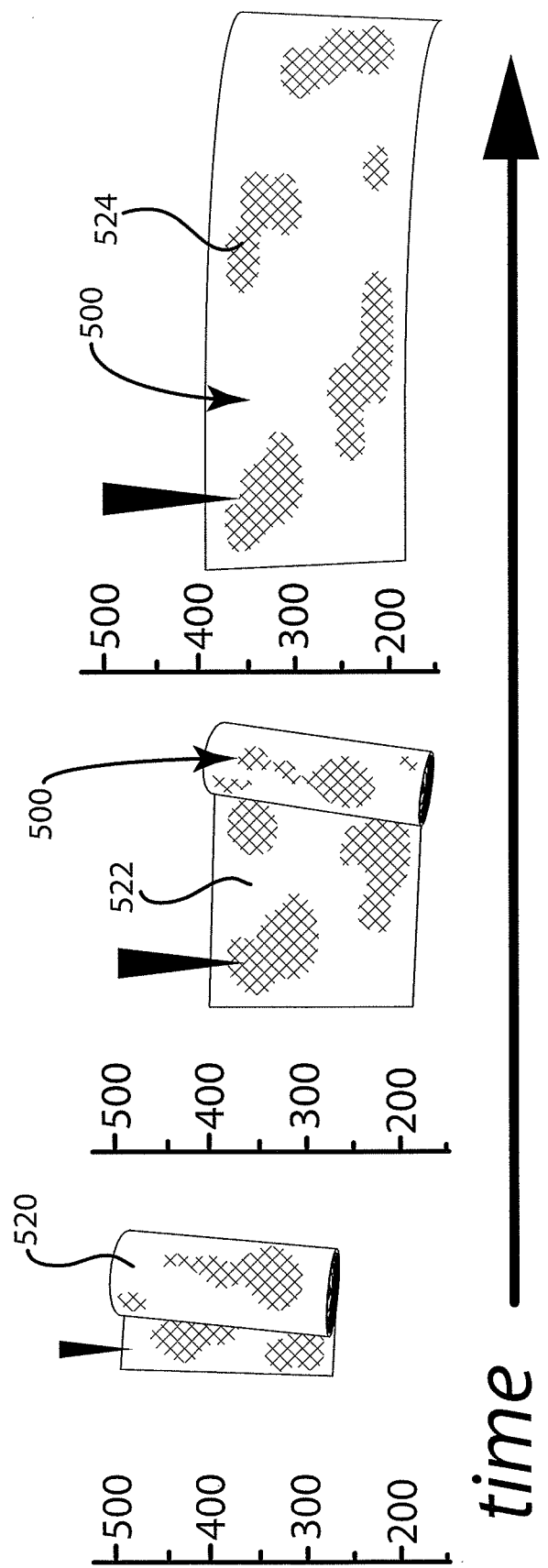
FIG. 7 is a schematic diagram of an SMP-integrated mesh from the rolled configuration to the fully deployed configuration over time.

Each mesh was then removed from the water bath and allowed to unroll without assistance, as shown n FIG. 7, during which the elapsed time was measured. Immediately upon removal from the 37° C. water bath, the SMP-integrated mesh 500 was in the rolled configuration 520. Over time, the SMP-integrated mesh 500 unrolled into the partially unrolled configuration 522 and then to the fully deployed configuration 524. The elapsed time until the SMP-integrated mesh 500 achieved the fully deployed configuration 524 is the time to unroll, measured in seconds and presented in Table 3. In a 37° C. water bath, as $T_g$ decreased towards 37° C., time to unroll decreased.

TABLE 3

|  | $T_g$ (° C.) | Time to Unroll (s) |
|---|---|---|
| Formula A | 57° C. | 113 |
| Formula B | 37° C. | 3 |
| Formula C | 47° C. | 23 |
| Formula D | 44° C. | 7 |

Example 7—In Vivo Testing of SMP-Integrated Fabrics

This study was conducted under a test protocol approved by the Institutional Animal Care and Use Committee (IACUC protocol 87,909(05)1D). A single live female swine was anesthetized and secured in a supine position. Several laparoscopic ports were inserted to perform experiments within the abdominal cavity. At the completion of testing, the animal was euthanized by anesthesia overdose.

Based on the results of DMA testing (see Example 2) and tensile testing (see Example 3), Formulas C and D (see Table 1) were chosen for the acute swine model test. Surgical meshes were placed in glass molds (100 mm×100 mm) in a flat configuration, and SMP solution was injected and subsequently cured using ultraviolet energy. After synthesis, SMP-integrated and unmodified surgical mesh specimens were cut to approximately 70 mm×70 mm to ensure uniform shape and size. The Formula C specimen had a thickness of 0.68 mm, and the Formula D specimen had a thickness of 1.0 mm. Final specimens were steam sterilized by a standard autoclave system.

Figure 8A:
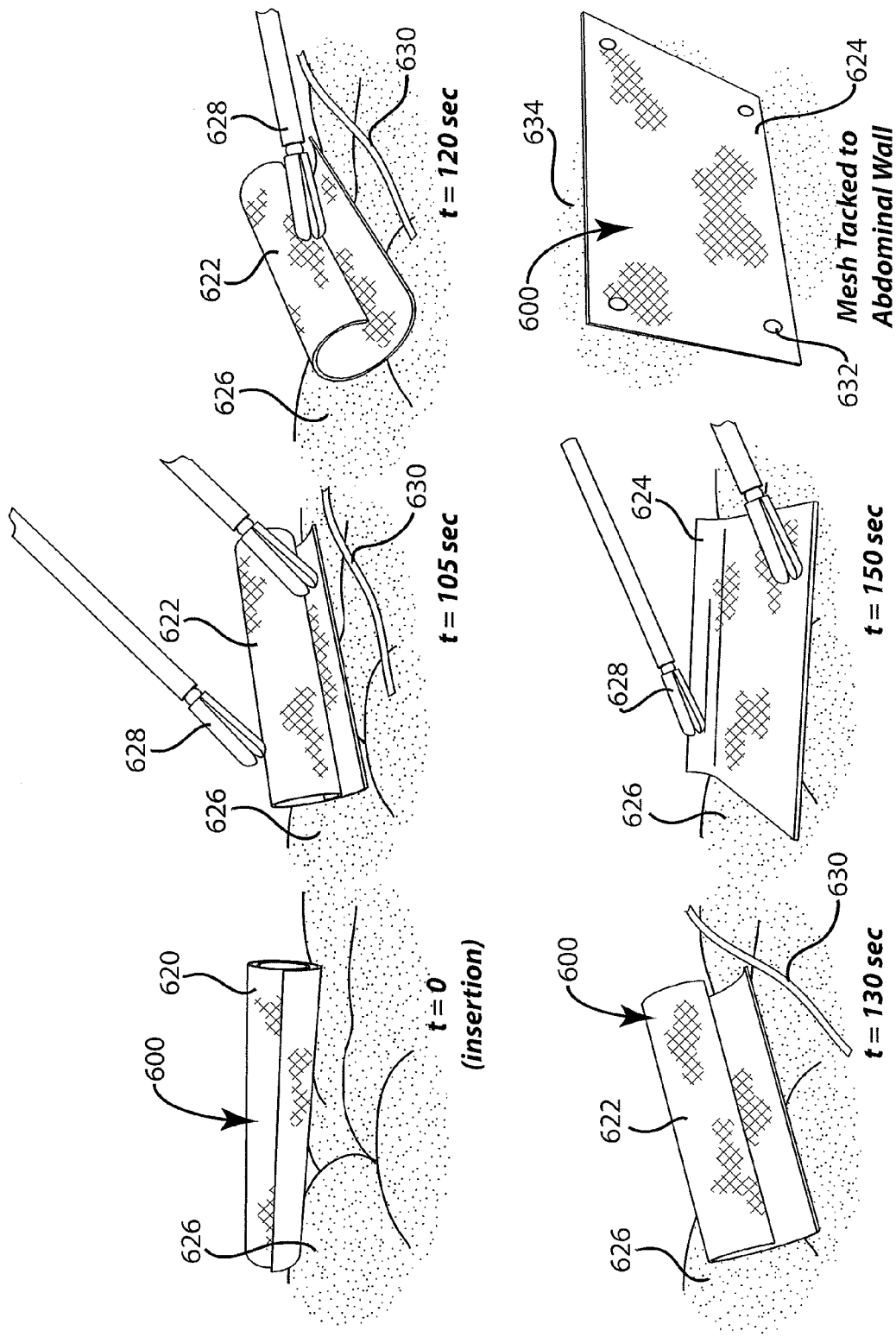
FIG. 8A is a schematic diagram of the intra-operative procedure of Example 7 using the Formula C SMP-integrated fabric of Table 1.
Figure 8B:
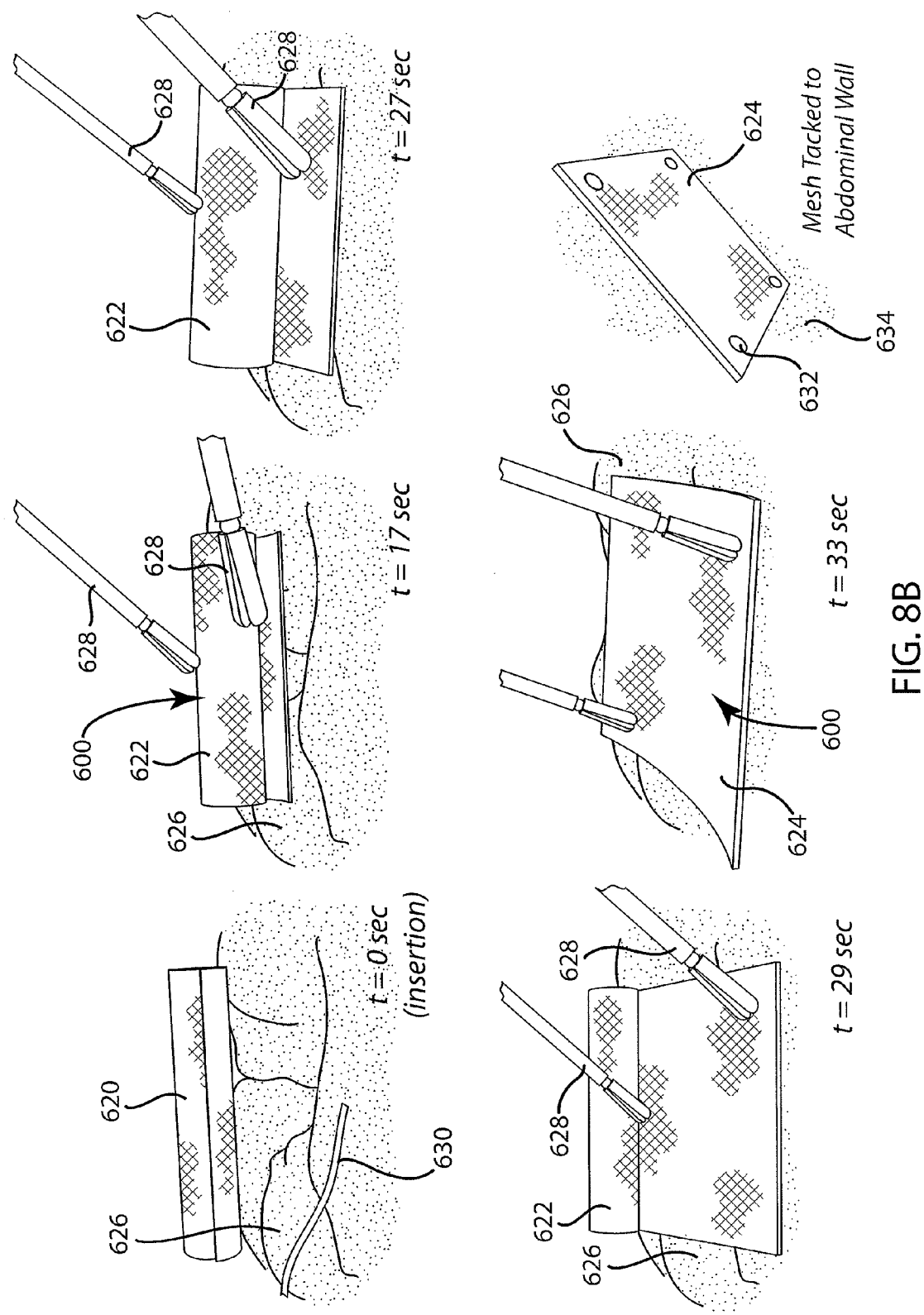
FIG. 8B is a schematic diagram of the intra-operative procedure of Example 7 using the Formula D SMP-integrated fabric of Table 1.

Referring now to FIGS. 8A and 8B, the surgical procedure involved placing one Formula C SMP-integrated mesh 600 specimen and one Formula D SMP-integrated mesh 600 specimen against the porcine abdominal wall 634 using a standard intraperitoneal laparoscopic approach. Intra-abdominal cavity temperature was monitored before insertion of each SMP-integrated mesh 600 using a thermometer 630 (HHSO6RA, Omega), and a temperature of 37.5° C. was noted. No peritoneal defect was created in this study. SMP-integrated meshes 600 were submerged in 50° C. sterile water, which allowed the SMP-integrated meshes 600 to be rolled into a configuration tight enough to fit into a 12 mm laparoscopic cannula port. The SMP-integrated meshes 600 were then cooled by submerging in sterile water at less than 20° C. The SMP-integrated meshes 600 retained the rolled configuration 620, and were inserted into the abdominal cavity of the swine using a 12 mm laparoscopic cannula port. The SMP-integrated mesh 600 was positioned on the intestines 626, and then observed for automatic unrolling as the temperature of the SMP-integrated mesh 600 increased to that of the abdominal cavity. Both SMP-integrated meshes 600 were secured using 5 mm tacks 632 (Protack, Covidien) at their four corners to evaluate feasibility of tack usage with added thickness of SMP. The thicker Formula D SMP-integrated mesh 600 was punctured twice using a suture grasper (Proxy Biomedical) to evaluate feasibility of penetration properties.

In the rolled configuration 620, both Formula C and Formula D SMP-integrated mesh 600 were easily inserted through the cannula port and manipulated using common laparoscopic tools 628, similar to an unmodified mesh. Upon insertion into the abdominal cavity, the Formula C SMP-integrated mesh 600 did not unroll automatically. After more than 100 seconds, the SMP-integrated mesh 600 was physically manipulated to achieve a partially unrolled configuration 622, and then a fully deployed configuration 624 within an additional 50 seconds (see FIG. 8A). The SMP-integrated mesh 600 was then tacked to the abdominal wall 634. Without being limited to any mechanism or mode of action, the 47° C. $T_g$ of Formula C is believed to have been too high to allow automatic unrolling in the approximately 37° C. environment of the porcine abdominal cavity.

The Formula D SMP-integrated mesh 600 unrolled automatically, and, compared to the Formula C SMP-integrated mesh 600, significantly less manipulation was required to achieve a partially unrolled configuration 622 and then a fully deployed configuration 624 by approximately 30 seconds (see FIG. 8B). Without being limited to any mechanism or mode of action, the 44° C. $T_g$ of Formula D is believed to have provided a better match for an average abdominal cavity temperature of 37.5° C. as compared to Formula D, which enabled the surgical mesh to automatically unroll. Automatic unrolling may improve mesh positioning, improve mesh placement, decrease surgical time, and/or decrease surgical complications.

Example 8—DMA and Uniaxial Tensile Testing of SMP-Integrated Fabrics

The results of Examples 1-7 demonstrated that it is possible to create SMP-integrated fabrics with highly tailorable features including thermally triggered deployment, precise control of deployment time, and precise control of mechanical stiffness. However, the varying results from the four formulations of Table 1 demonstrated that the individual chemical components, their percent weight contribution, and even the molecular weight of the same component (PEGDMA) could have dramatic and unexpected effects on $T_g$, tensile strength, and strain to failure (see Table 2). Thus, it was difficult to predict which SMP formulation would possess qualities such as flexibility and deformability with the mesh, while also possessing a target $T_g$ and sufficient tensile strength.

In order to further improve upon the performance of the SMP formulations of Table 1, additional SMP formulations were prepared using a wider range of chemical components than in Table 1: tBA, nBA, isobutyl acrylate (iBA), ethylhexyl acrylate (EHA), PEGDMA at three different molecular weights, and urethane diacrylate. The formulations were prepared as in Example 1, and the percent composition of each ingredient by weight is presented in Table 4. $T_g$ was determined as in Example 2 and uniaxial tensile tests were performed as in Example 3. The $T_g$ and strain-to-failure results are presented in Table 4.

TABLE 4

| Formula | tBA (%) | nBA (%) | PEGDMA 550 (%) | PEGDMA 750 (%) | PEGDMA 1000 (%) | iBA (%) | EHA (%) | Urethane diacrylate (%) | Tg (° C.) | Avg. Strain (mm) |
|---|---|---|---|---|---|---|---|---|---|---|
| O | 90 | | | | 10 | | | | 54 | >45 |
| A | 80 | | 20 | | | | | | 57 | 28.59 |
| B | 65 | 15 | 20 | | | | | | 37 | 9.93 |
| C | 75 | 10 | 15 | | | | | | 47 | 18.85 |
| D | 80 | | | | 20 | | | | 44 | 31.85 |
| E1 | 77 | | | | 23 | | | | 40 | 18.73 |
| E2 | 77 | | | | 23 | | | | 40 | 18.31 |
| F | 78 | | | | 22 | | | | 41 | 21.28 |
| G | 76 | 4 | | | 20 | | | | 38 | 20.05 |
| H | 76 | 4 | | 2 | 18 | | | | 35 | 18.27 |
| J | 75 | 5 | | 1 | 19 | | | | 36 | 20.01 |
| K | 80 | | | | 15 | | | 5 | 47 | 37.62 |
| L | 76 | | | | 19 | | | 5 | 42 | 23.60 |
| M | 79 | | | | 19 | 2 | | | 40 | 26.98 |
| N | 79 | | | | 19 | | 2 | | 43 | 26.43 |
| P | 78 | | | | 15 | 3.5 | 3.5 | | 43 | 31.63 |

Example 9—Porous and Non-Porous SMP-Modified Fabric Meshes

Figure 3B:
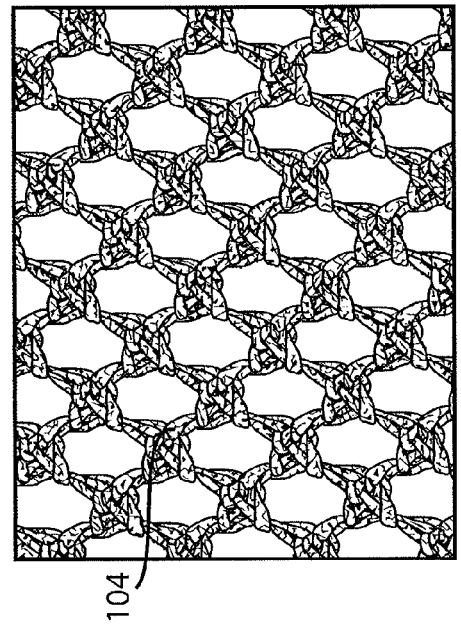
FIG. 3B is a schematic diagram of an SMP-integrated medical fabric of FIG. 1B in which the medical fabric retains its porosity.

Porous SMP-integrated meshes were prepared according to Example 1 with the following modifications. SMP Formula F according to Table 4 in Example 8 was applied to PETKM7001 (Textile Development Associates) commercially available polyester medical mesh fabrics. Meshes were placed in glass molds (100 mm×100 mm), molds were purged with nitrogen gas, SMP solution was injected to coat the mesh fibers, and the excess SMP solution was drained from the mold. The mold was continually purged with nitrogen gas during the polymerization process, which helped to prevent oxygen inhibition. A 365 nm UV lamp (Dymax 2000-PC), which provided approximately 15-25 mW/cm² at the mold surface, was pulsed on and off every 30 seconds for a total exposure time of 20 minutes to cure the meshes. The resulting SMP-integrated mesh 100 is shown in FIG. 3B. The original pore size of the unmodified medical mesh fabric 104 (see FIG. 3A) was maintained using this process. The approximate thickness of the porous SMP-integrated mesh 100 was 0.70 mm. The approximate thickness of the unmodified mesh 104 was 0.35 mm.

Non-porous (i.e., fully coated) SMP-integrated meshes were produced by filling the mold with SMP Formula F, which yielded a mesh embedded in SMP Formula F. The approximate thickness of the non-porous SMP-integrated mesh was 1.0 mm.

Example 10—Dynamic Mechanical Analysis of SMP-Integrated Fabric Meshes

DMA was performed on SMP Formula F of Table 4, on the porous Formula F SMP-integrated mesh of Example 9, and on unmodified mesh according to the procedure described in Zimkowski et al. (J Biomed Mater Res A. 2013; 2613-20). Meshes were cut into strips approximately 25 mm×5.5 mm×1 mm. A TA Q800 DMA was used with cyclic strain control set at 0.1% strain and frequency at 1.0 Hz. DMA samples were characterized by storage modulus and the tan delta curve. $T_g$ was determined to be the peak of the tan delta curve.

Figure 9A:
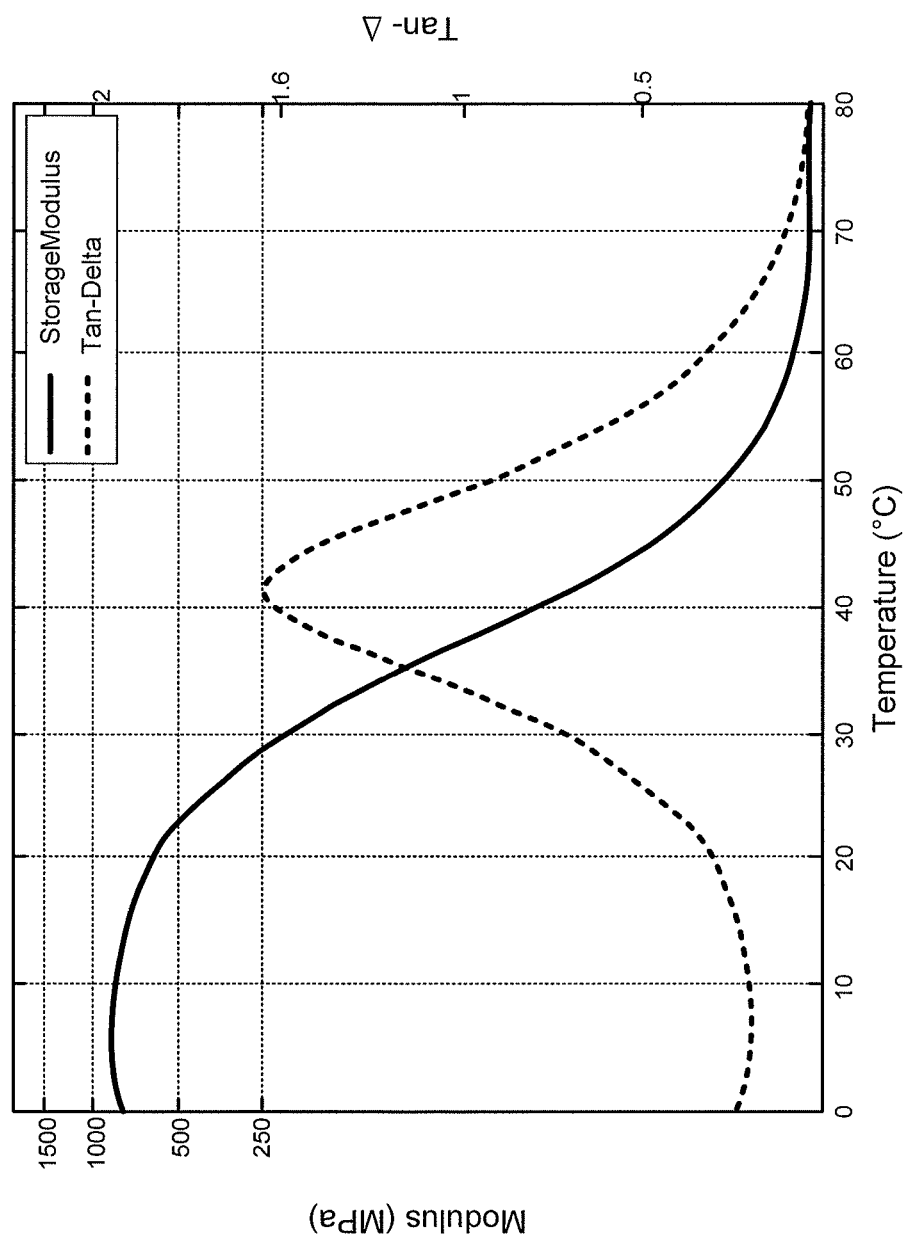
FIG. 9A is a graph of the dynamic mechanical analysis of SMP Formula F of Example 10.
Figure 9B:
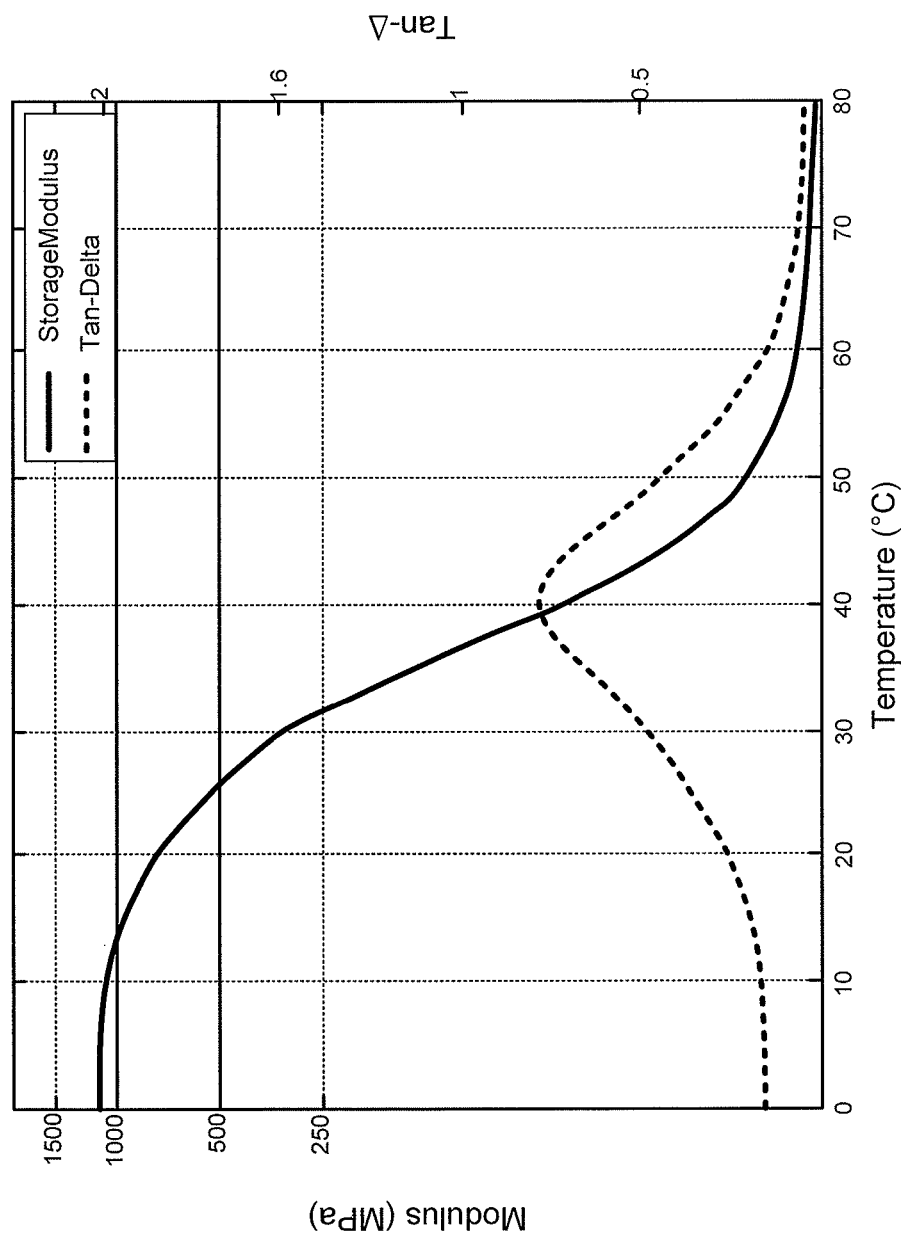
FIG. 9B is a graph of the dynamic mechanical analysis in the lengthwise direction of Formula F SMP-integrated fabric.
Figure 9C:
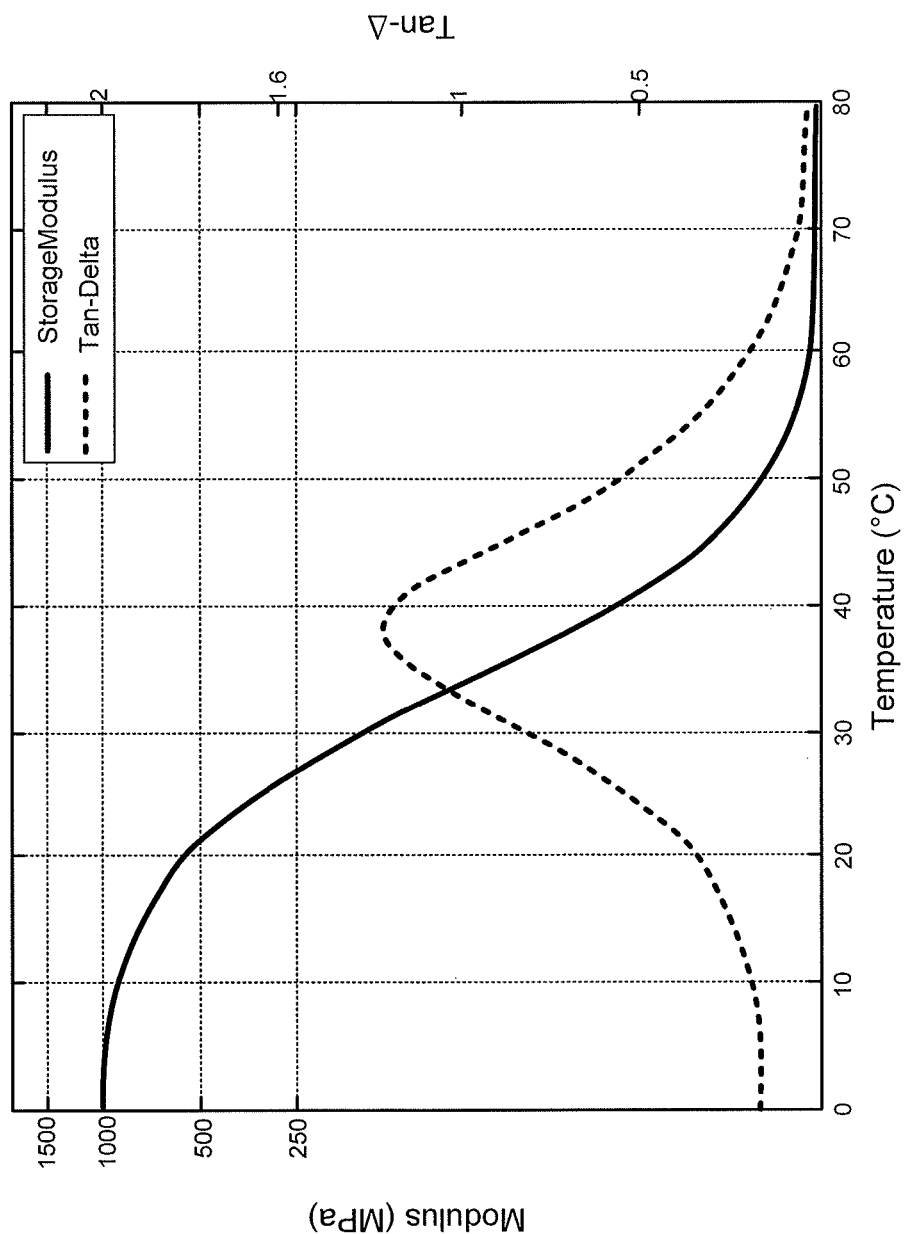
FIG. 9C is a graph of the dynamic mechanical analysis in the widthwise direction of Formula F SMP-integrated fabric.

Results are presented in FIGS. 9A-9C. FIG. 9A demonstrates that SMP Formula F had a $T_g$ of 41.5+/−0.7° C. FIG. 9B demonstrates that the porous SMP-integrated mesh of Example 9 tested in lengthwise direction had a $T_g$ of 41.0+/−1.0° C. FIG. 9C demonstrates that the porous SMP-integrated mesh tested in widthwise direction had a $T_g$ of 36.4+/−2.6° C. The similarities of $T_g$ across the DMA samples demonstrate that the mesh had a minimal effect on native SMP T characteristics.

Example 11—Cytotoxicity Tests

Non-porous SMP-integrated meshes were produced according to Example 9 with each of SMP Formulas F, M, and P of Table 4. Cytotoxicity testing was performed using the following ISO 10993-5:2009-compliant MEM elution method. The SMP-integrated meshes were sterilized by autoclave, and 30 cm² were extracted in 10 mL of Eagle's MEM media+5% fetal bovine serum (a ratio of 60 cm² per 20 mL) at 37° C. for 24 hours. Each media was inoculated into an L-929 mouse fibroblast cell line, and the cells were incubated at 37° C.

Cell cultures were evaluated for cytotoxic effects by microscopic observation after 24-, 48-, and 72-hour incubation periods. Cytotoxic effects included morphologic changes in cells, such as granulation, crenation, or rounding, and loss of viable cells from the monolayer by lysis or detachment. Cells were scored according to ISO standards. Briefly, cells are scored from 0 to 4, wherein 0 indicates no reactivity, no cell lysis, and no reduction of cell growth, and 4 indicates severe reactivity and nearly complete destruction of cell layers. An eluted SMP-integrated mesh with a score of 0, 1, or 2 was non-toxic, and an eluted SMP-integrated mesh with a score of 3 and 4 was toxic.

Results are presented in Table 5. All SMP Formulas were non-toxic at all time points. Cells incubated with SMP Formulas F and M did not demonstrate morphologic changes or loss of viable cells at any time point. Cells incubated with SMP Formula P demonstrated little to no reduction in cell growth and cell lysis.

TABLE 5

| SMP Formula | Score (24/48/72 h) |
|---|---|
| F | 0/0/0 |
| M | 0/0/0 |
| P | 0/1/1 |

Example 12—Acute Large Animal Study

The porous and non-porous Formula F SMP-integrated meshes of Example 9, and unmodified mesh, were used in an intraperitoneal laparoscopic surgical study in a porcine model (IACUC protocol 87912(04)1D). A single live female pig weighing approximately 55 kg was anesthetized using ketamine and xylazine for induction and isoflurane for maintenance. The animal was secured in a supine position, and several laparoscopic ports were inserted into the abdominal cavity. Following the study, the animal was euthanized using sodium pentobarbital.

Figure 10:
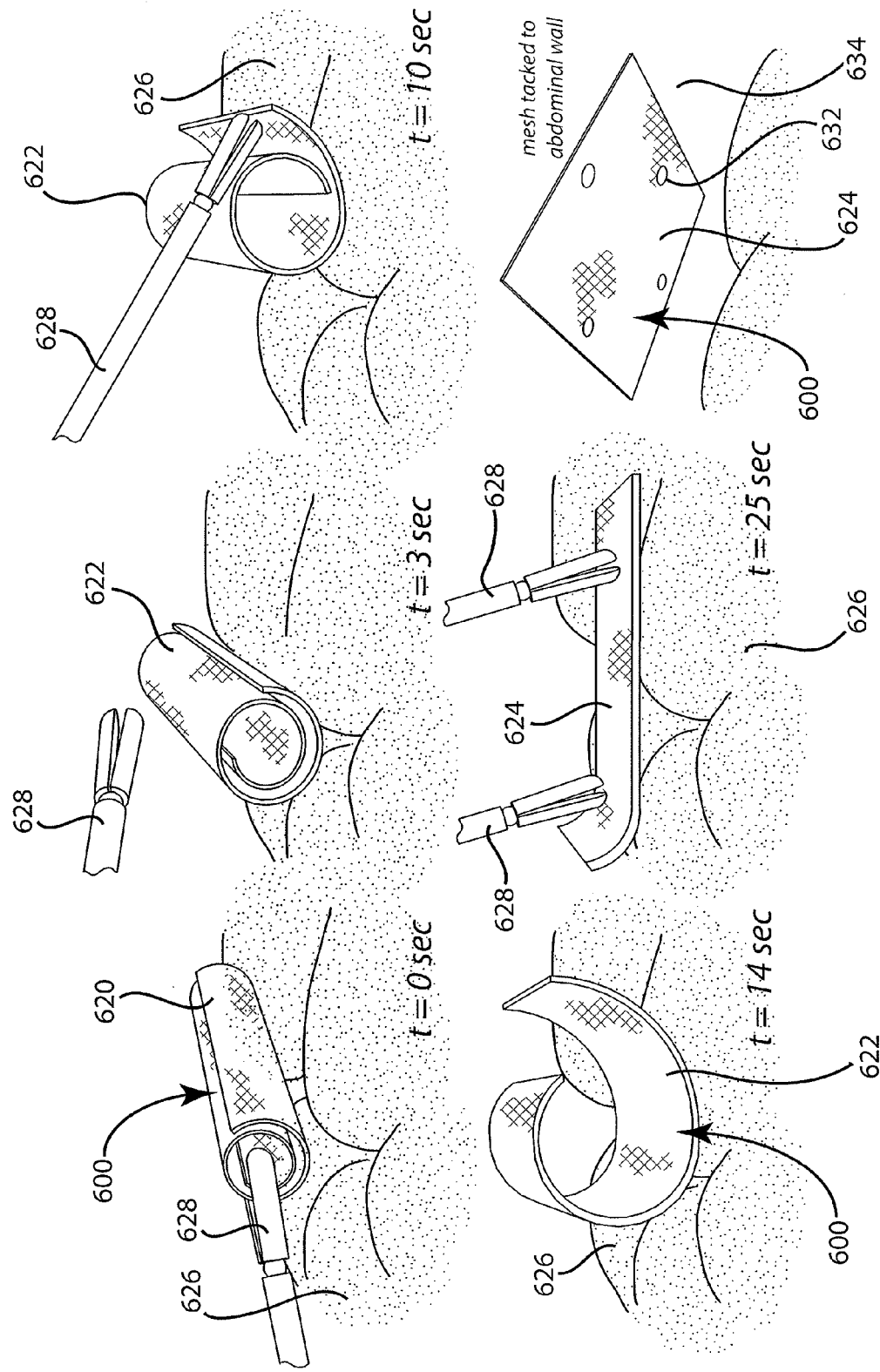
FIG. 10 is a schematic diagram of the intra-operative procedure of Example 12 using non-porous Formula F SMP-integrated fabric.
Figure 11:
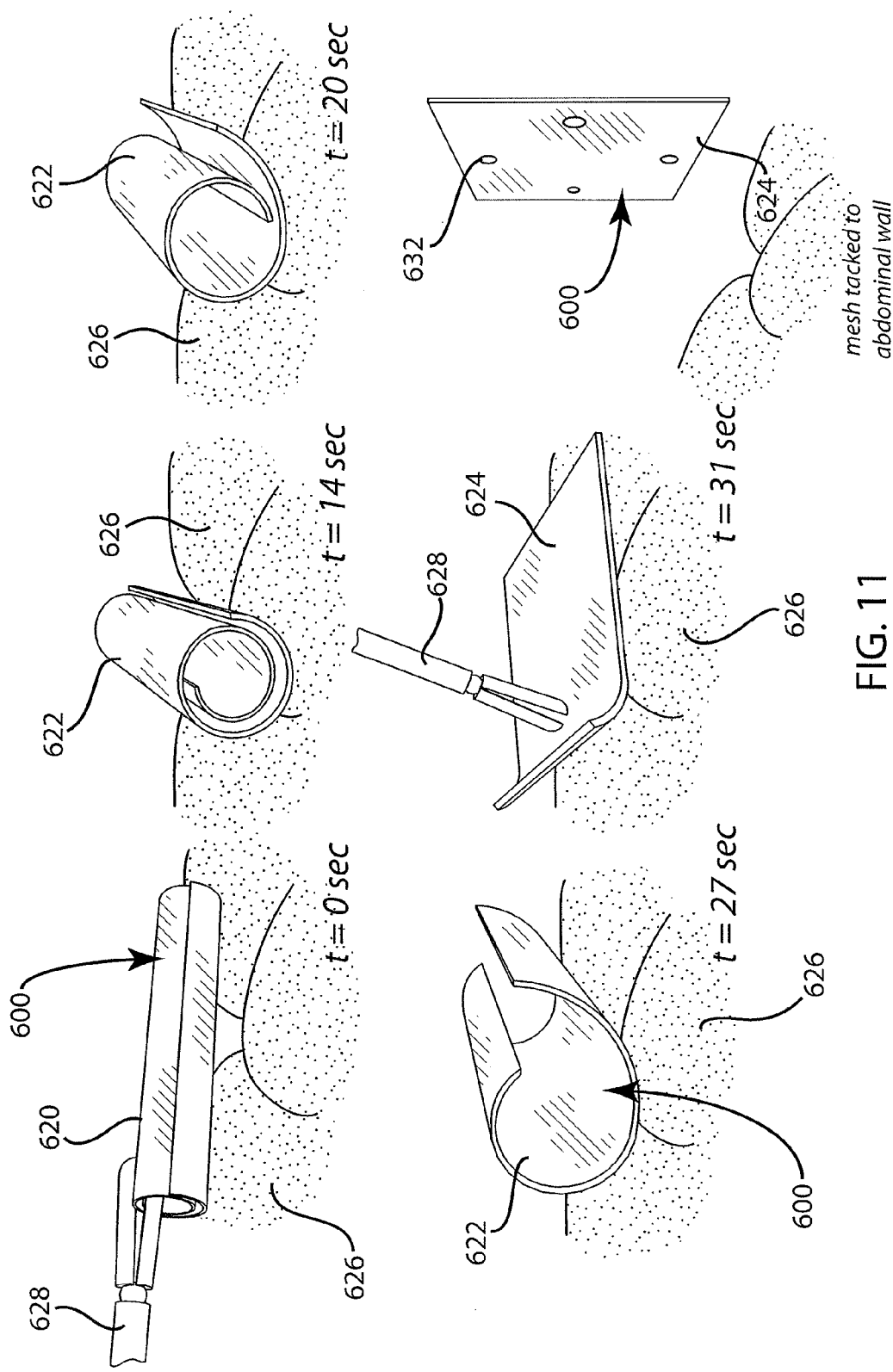
FIG. 11 is a schematic diagram of the intra-operative procedure of Example 12 using porous Formula F SMP-integrated fabric.

With reference to FIGS. 10 & 11, each of the non-porous and porous Formula F SMP-integrated meshes 600a, 600b of Example 9, and the unmodified mesh (not shown), were surgically placed according to the procedure of Zimkowski et al (supra) and Example 7. Briefly, meshes were cut into 80 mm×80 mm pieces. The SMP-integrated meshes 600 were submerged in water heated to approximately 60° C., rolled to fit into a cannula port, and cooled by submerging in water cooled to approximately 20° C. Each SMP-integrated mesh 600 retained a rolled configuration 620 once cooled, and was inserted into the porcine abdominal cavity using a 12 mm laparoscopic cannula port, and manipulated for placement. The unmodified mesh was similarly inserted. Each mesh was secured to the abdominal wall 634 using 5 mm tacks 632 (Protack, Covidien). No peritoneal defect was created. Mesh unrolling time was measured throughout the procedure.

In the rolled configuration 620, each mesh was easily inserted through the cannula port and manipulated using common laparoscopic tools 628. Unrolling and placement of the non-porous SMP-integrated mesh 600a is presented in FIG. 10. Upon insertion into the abdominal cavity, the non-porous SMP-integrated mesh 600a automatically obtained a partially unrolled configuration 622 within 3 seconds (see upper middle panel), and continued to automatically unroll with little manipulation until it reached the fully deployed configuration 624 in approximately 25 seconds (see lower middle panel).

Unrolling and placement of the porous SMP-integrated mesh 600b is presented in FIG. 11. Upon insertion into the abdominal cavity, the porous SMP-integrated mesh 600b automatically obtained a partially unrolled configuration 622 within 14 seconds (see upper middle panel), and continued to automatically unroll with little manipulation until it reached the fully deployed configuration 624 in approximately 31 seconds (see lower middle panel).

Thus, the non-porous SMP-integrated mesh 600a unrolled 9% faster than the porous SMP-integrated mesh 600b, but the difference had minimal impact on in vivo placement and tacking. Comparable performance between non-porous and porous SMP-integrated meshes 600 demonstrates that minimal amounts of SMP may be used to achieve the desired automatic unrolling and tissue ingrowth properties.

In contrast to the SMP-integrated meshes 600, the unmodified mesh unrolled in 65 seconds and required more manipulation and positioning. Results demonstrate that the SMP-integrated meshes 600 unrolled in an automatic, body temperature-activated manner, and more than twice as quickly as the unmodified mesh. Automatic unrolling may improve mesh positioning, improve mesh placement, decrease surgical time, and/or decrease surgical complications.

Example 13—Chronic Small Animal Study

The porous Formula F SMP-integrated mesh of Example 9, and unmodified mesh, were used in a surgical study in a rat model (IACUC protocol 43812(08)1D) according to a modified protocol of Horan et al. (HERNIA. 2009 April; 13(2):189-99).

Briefly, four female Sprague Dawley rats (Charles River Laboratories) weighing approximately 310-370 g were anesthetized using ketamine and xylazine or inhaled isoflurane. Carprofen was administered subcutaneously for pain relief on the day of surgery, and for two days post-surgery.

Figure 12B:
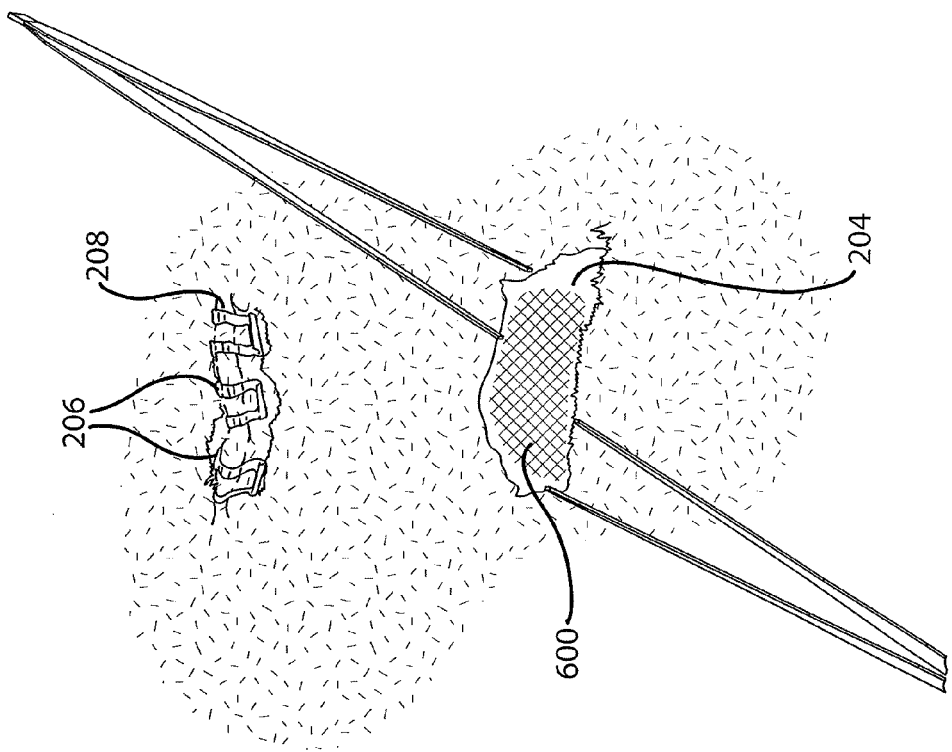
FIG. 12B is schematic diagram of the mesh-insertion and wound-closing steps of the intra-operative procedure of Example 13.
Figure 12A:
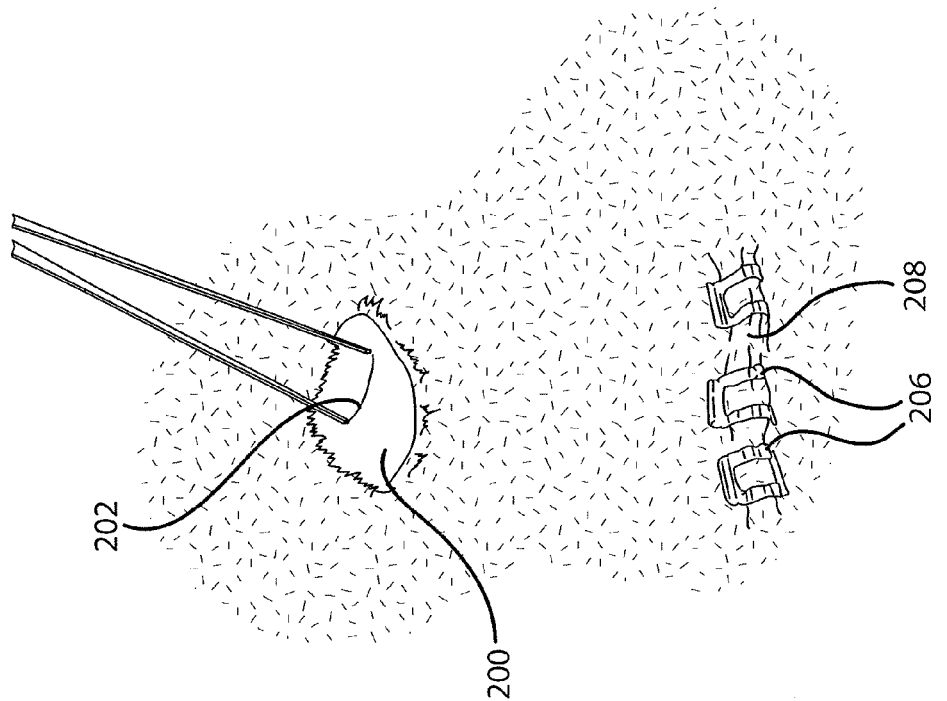
FIG. 12A is schematic diagram of the puncture-forming step of the intra-operative procedure of Example 13.

With reference to FIG. 12, each anesthetized animal was placed in a supine position, and the skin was surgically dissected to expose the abdominal muscle wall 200 underneath. A scalpel was used to create two punctures 202 (0.5 cm×1 cm or smaller) on each side of the abdominal muscle wall 200, inferior to the rib cage and superior to the pelvis (see FIG. 12A). Pieces of mesh approximately 1 cm×2 cm were implanted subcutaneously over the punctures 202. The porous SMP-integrated mesh 600 was centered over the left-side puncture 202, and the unmodified mesh was centered over the right-side puncture 202. Each piece was secured to the abdominal muscle wall 200 using non-absorbable sutures 204 (see FIG. 12B). The openings in the skin were closed over the meshes using sutures 204 and surgical clips 206 (see FIG. 12B) to form closed wounds 208.

Figure 13:
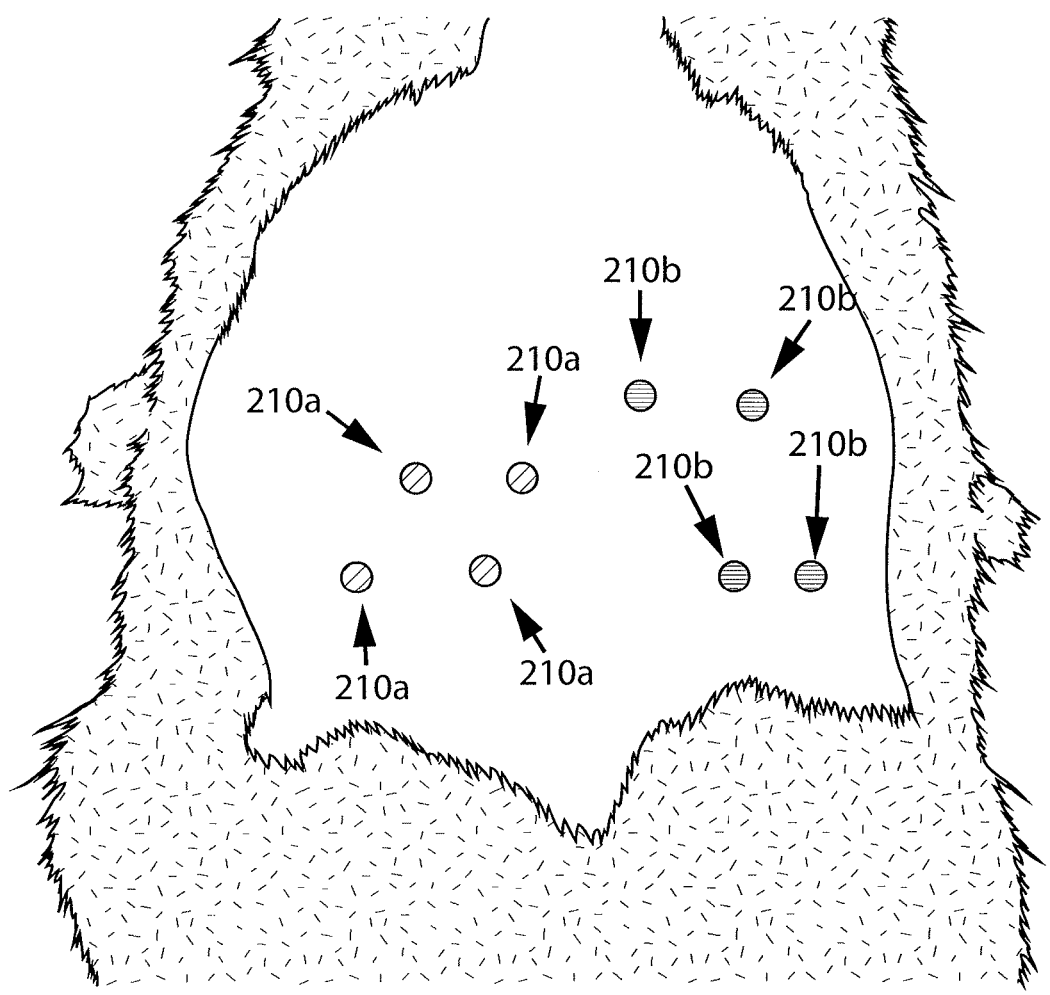
FIG. 13 is a schematic diagram of a rat abdomen 30 days after the intra-operative procedure of Example 13.

All four animals survived to the end of the study (30-33 days). No outward signs of infection or complications were observed. An anterior view of a shaved rat abdomen after 30 days post-surgery is shown in FIG. 13. The sutures 210a securing the unmodified mesh are shown on the left side of the figure, and the sutures 210b securing the SMP-integrated mesh are shown on the right side of the figure. The SMP-integrated mesh demonstrated noticeably less contraction than the unmodified mesh. Thus, the SMP-integrated mesh is beneficial for hernia repair because excessive contraction can contribute to hernia recurrence.

Example 14—Histology Studies with Hematoxylin and Eosin Staining

The rats of Example 13 were euthanized by carbon dioxide asphyxiation after 30-33 days, and all abdominal wall tissue surrounding the implanted meshes was harvested. Dissected tissue samples were fixed in a phosphate buffered saline formalin solution. Transverse tissue cross-sections, including epidermis through muscle wall, were embedded in paraffin. Slide samples were cut with a microtome and were stained with hematoxylin and eosin.

Figure 14:
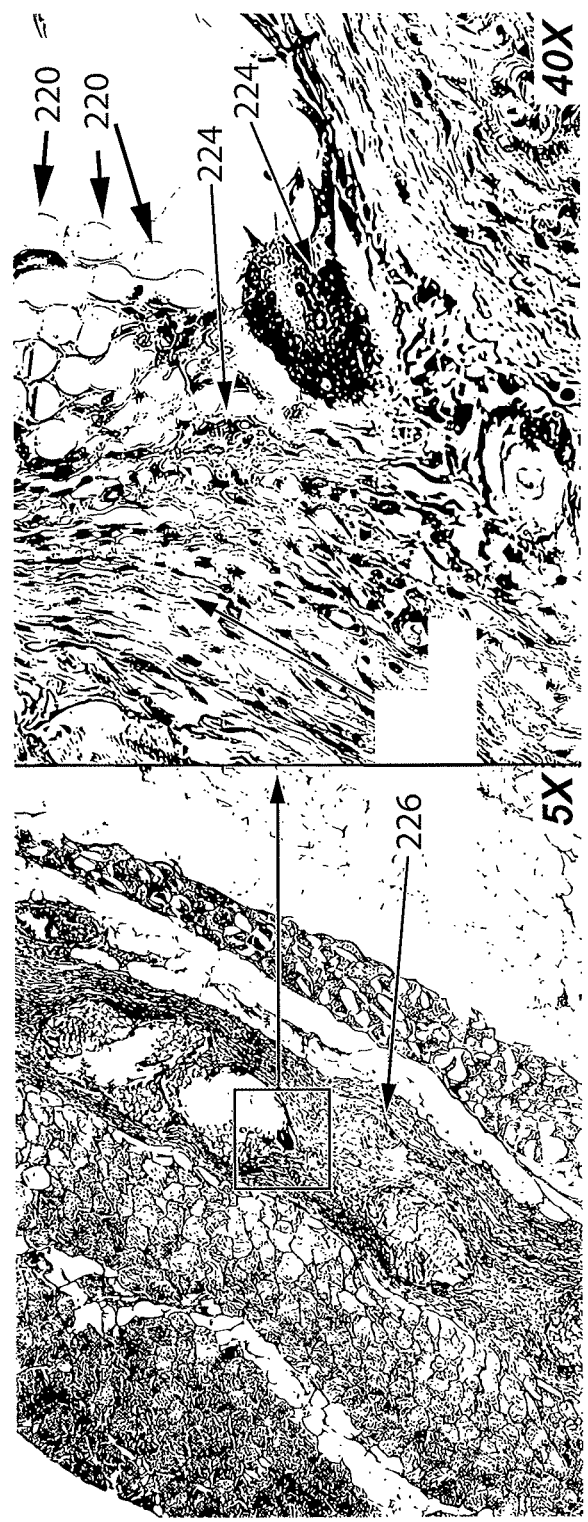
FIG. 14 is a schematic diagram of local tissue reaction to the unmodified fabric of Example 14.
Figure 15:
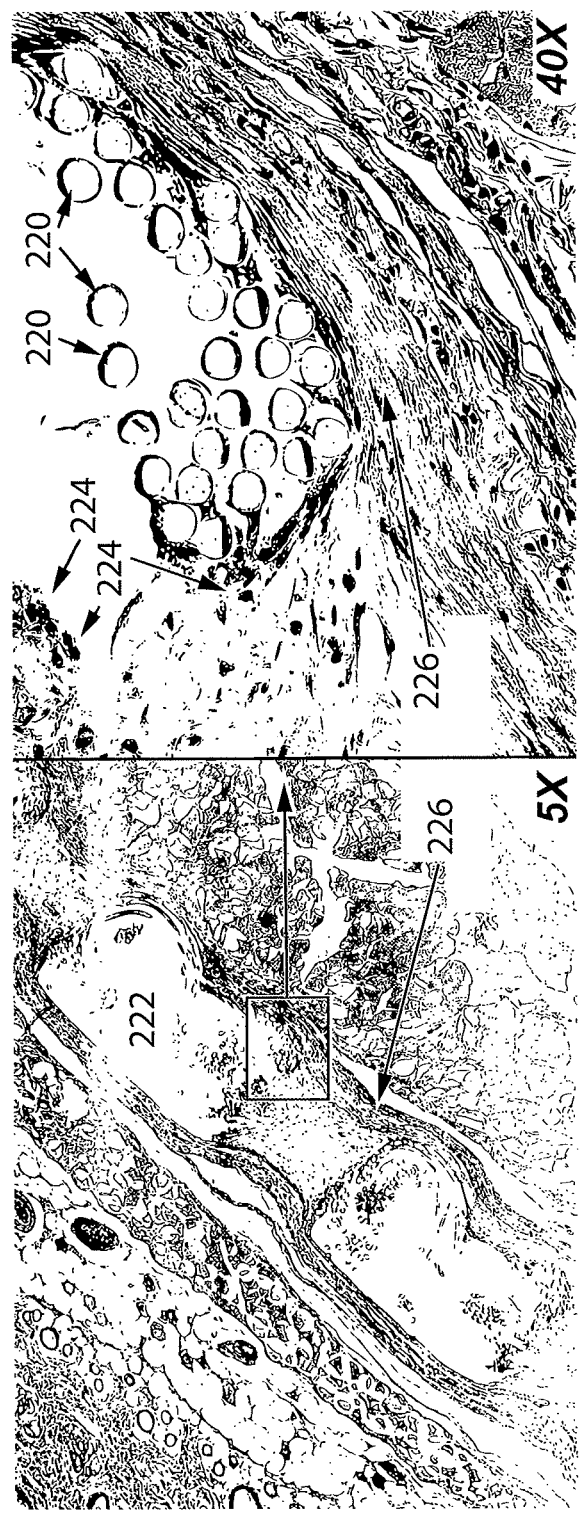
FIG. 15 is a schematic diagram of local tissue reaction to the SMP-integrated fabric of Example 14.

Results of hematoxylin- and eosin-stained tissues are presented in FIGS. 14 and 15. Mesh fibers 220, shape memory polymers 222, and foreign body giant cells 224 are shown. FIG. 14 shows local tissue reaction to the unmodified mesh, and FIG. 15 shows local tissue reaction to the SMP-integrated mesh.

The tissue around the unmodified mesh and the SMP-integrated mesh demonstrated similar fibrous encapsulation 226, presence of foreign body giant cells 224, and tissue ingrowth into the mesh fibers 220 and pores. Tissue ingrowth can be beneficial to hernia repair, and the results demonstrate that SMP integration did not decrease tissue ingrowth into the mesh compared to control unmodified mesh. Also, SMP integration did not increase the inflammatory response over implantation of control unmodified mesh.

Example 15—Mechanisms of Tissue Ingrowth

Figure 16A:
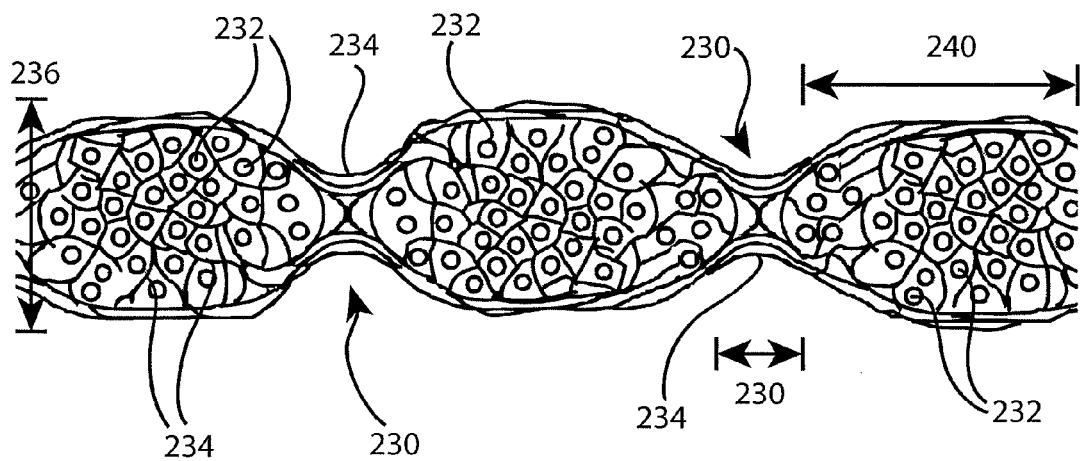
FIG. 16A is a schematic diagram of a possible mechanism of tissue ingrowth into an unmodified fabric.
Figure 16B:
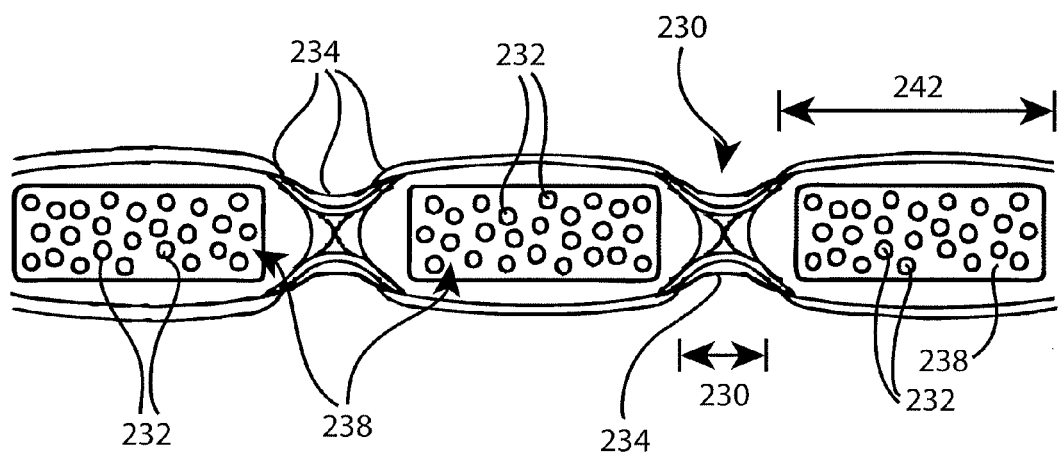
FIG. 16B is a schematic diagram of a possible mechanism of tissue ingrowth into an SMP-integrated fabric.

FIG. 16A depicts one possible mechanism for tissue ingrowth into an unmodified mesh 240 and FIG. 16B depicts one possible mechanism for tissue ingrowth into an SMP-integrated mesh 242.

In FIG. 16A, inflammatory cells and fibroblasts migrate through mesh pores 230 and between individual mesh fibers 232 of unmodified mesh 240, separating individual mesh fibers 232 from the weave. Collagen Type I and Type III fibers 234 are laid down and bind the mesh 240 to surrounding tissue. A scar 236 encapsulates the unmodified mesh 240.

In FIG. 16B, the SMP 238 has coated and penetrated the mesh fibers 232, which binds them together and prevents cellular infiltration into individual fabric strands. Without cellular infiltration, collagen 234 cannot be laid down between individual mesh fibers 232, but collagen 234 ingrowth does occur through pores 230. Reduction in the amount of cellular migration through individual mesh fibers 232 decreases scar 236 thickness. Reinforcing strength is not sacrificed because tissue ingrowth between pores 230 is comparable between unmodified mesh 240 and SMP-modified mesh 242.

Example 16—Histology Studies with Picrosirius Red Staining

Tissue samples were prepared according to the protocol of Example 15 except that they were stained with Picrosirius Red to visualize collagen ingrowth into the implanted meshes.

Figure 17:
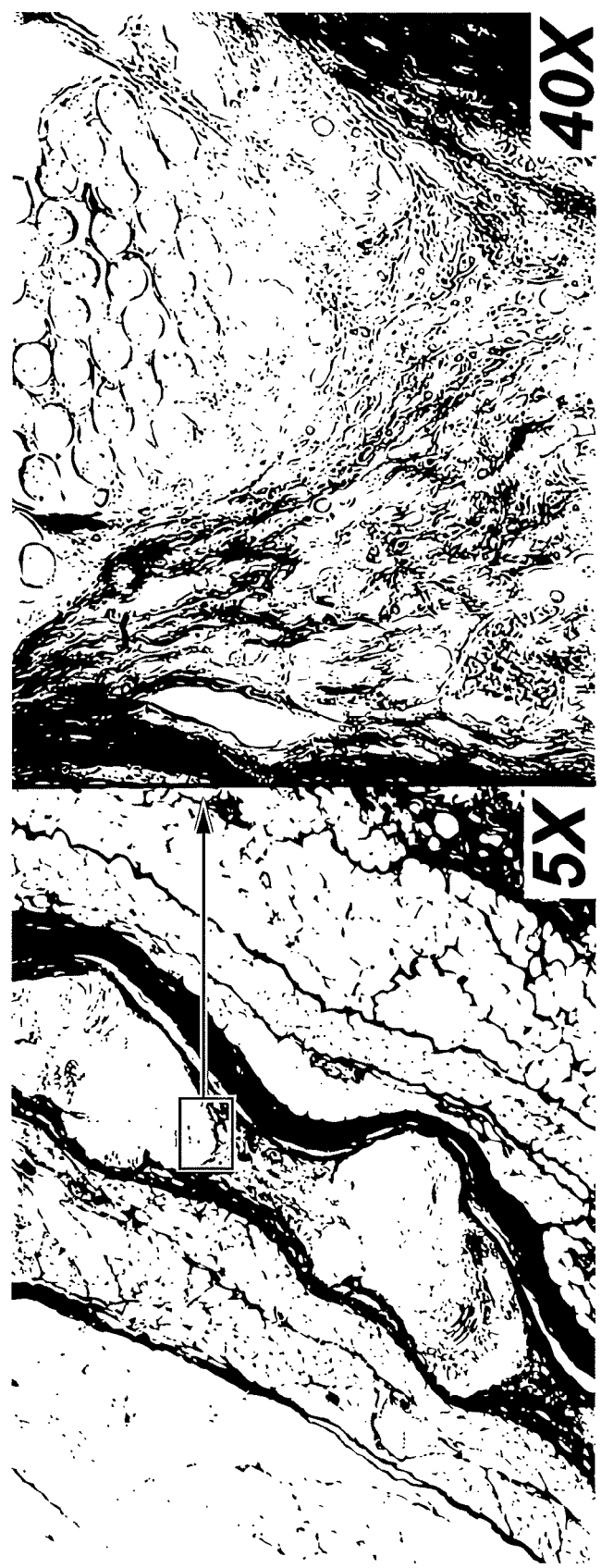
FIG. 17 is a schematic diagram of collagen ingrowth into the unmodified fabric of Example 16.
Figure 18:
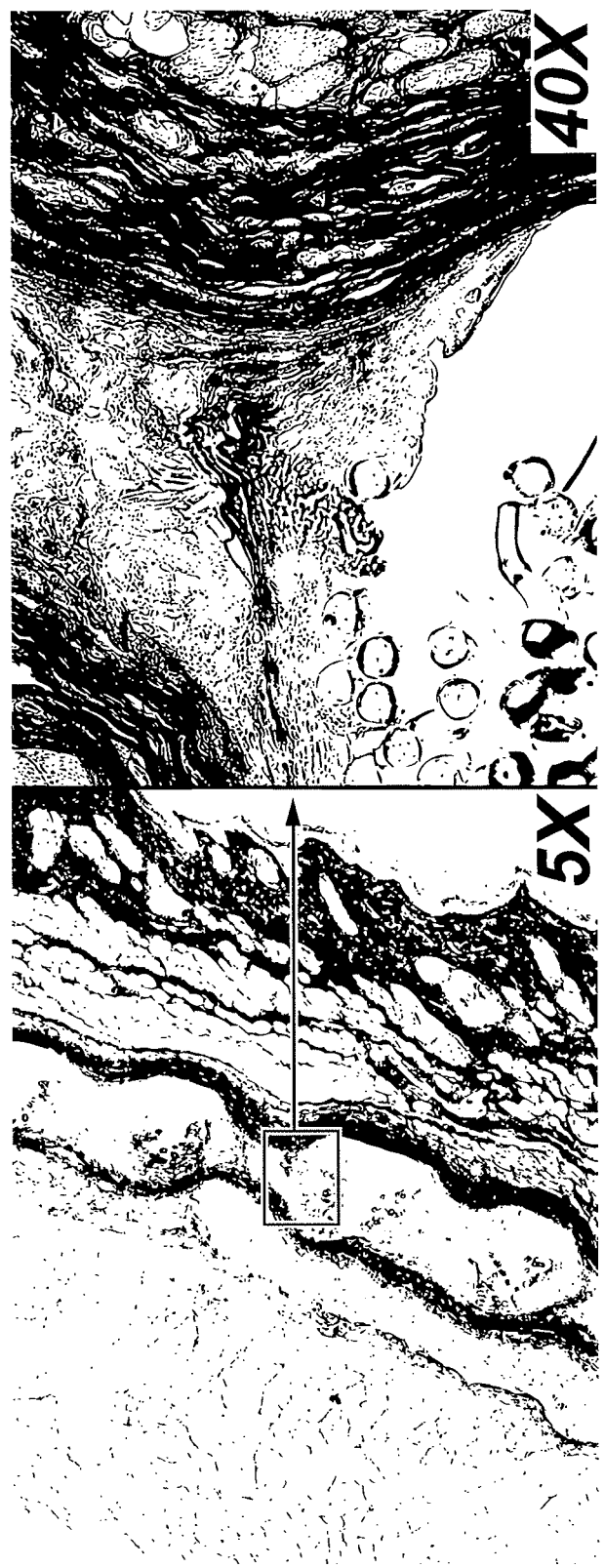
FIG. 18 is a schematic diagram of collagen ingrowth into the SMP-integrated fabric of Example 16.

Results are presented in FIGS. 17 (unmodified mesh) and 18 (SMP-integrated mesh). The results support the possible mechanisms of tissue ingrowth described in Example 15. In the unmodified mesh (FIG. 17), individual woven mesh stands were separated, and collagen fibers were laid down through the mesh. By comparison, FIG. 18 demonstrates that collagen ingrowth occurred only between the pores of the SMP-integrated mesh, but not through individual mesh strands.

Tissue ingrowth between pores was comparable between unmodified mesh and SMP-modified mesh. The SMP-integrated mesh contracted less than the unmodified mesh, and the SMP-modified mesh created a thinner scar than that of the unmodified mesh. SMP-integrated mesh is thus beneficial for hernia repair because it can produce an equally reinforced surgical site compared to unmodified mesh, but with a thinner, less noticeable scar.

All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. The exemplary drawings are for purposes of illustration only and the dimensions, positions, order and relative sizes reflected in the drawings attached hereto may vary.

The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the spirit or scope of this invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. A shape memory polymer integrated fabric comprising a shape memory polymer comprising 65-90 wt % tert-butyl acrylate, 10-28 wt % PEGDMA Mn=1000, 0.2-0.3 wt % 2,2 dimethoxy-2-phenylacetopenone, and at least one acrylate polymer; and
   a medical mesh fabric; wherein
   the shape memory polymer is integrated into the medical mesh fabric, and
   the shape memory polymer integrated fabric has a strain to failure of 15-20 mm.

2. The shape memory polymer integrated fabric of claim 1, wherein the shape memory polymer further comprises 1-10 wt % urethane diacrylate.

3. The shape memory polymer integrated fabric of claim 1, wherein the shape memory polymer further comprises 0.5-4 wt % ethylhexyl acrylate.

4. The shape memory polymer integrated fabric of claim 1, wherein the shape memory polymer further comprises 0.5-4 wt % isobutyl acrylate.

5. The shape memory polymer integrated fabric of claim 1, wherein the shape memory polymer further comprises 0.5-7 wt % urethane diacrylate and 0.5-7 wt % ethylhexyl acrylate.

6. The shape memory polymer integrated fabric of claim 1, wherein the shape memory polymer further comprises 0.5-2 wt % PEGDMA with a Mn=750 and 1-10% butyl acrylate.

7. The shape memory polymer integrated fabric of claim 1, wherein the PEGDMA is present at 15-25 wt %.

8. The shape memory polymer integrated fabric of claim 1, wherein the PEGDMA is present at 10-20 wt %.

9. The shape memory polymer integrated fabric of claim 1, wherein the shape memory polymer has a glass transition temperature of 34-48° C.

10. The shape memory polymer integrated fabric of claim 1, wherein the shape memory polymer has a glass transition temperature of 37-45° C.

11. The shape memory polymer integrated fabric of claim 1, wherein the shape memory polymer has a glass transition temperature of 35-41° C.

12. A method of surgically repairing a hernia comprising
   inserting the shape memory polymer-integrated fabric of claim 1 into an abdominal cavity; and
   securing the shape memory polymer-integrated mesh to a herniated abdominal wall.

13. The method of claim 12, further comprising
   heating the shape memory polymer-integrated fabric,
   rolling the shape memory polymer-integrated fabric for insertion into a cannula port, and
   unrolling the shape memory polymer-integrated fabric after inserting it into the abdominal cavity.

14. The method of claim 13, wherein the unrolling is temperature activated.

* * * * *